(12) United States Patent
Shanklin et al.

(10) Patent No.: US 6,974,893 B2
(45) Date of Patent: Dec. 13, 2005

(54) ISOFORM OF CASTOR OLEATE HYDROXYLASE

(75) Inventors: John Shanklin, Shoreham, NY (US); Edward J. Whittle, Greenport, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 477 days.

(21) Appl. No.: 10/185,578

(22) Filed: Jun. 28, 2002

(65) Prior Publication Data

US 2003/0079249 A1 Apr. 24, 2003

Related U.S. Application Data

(60) Provisional application No. 60/302,801, filed on Jun. 29, 2001.

(51) Int. Cl.$^7$ ........................... A01H 5/00; C12N 15/82
(52) U.S. Cl. ..................... 800/281; 800/298; 435/419; 435/468; 435/471; 435/252.3
(58) Field of Search ............................... 800/278, 281, 800/298; 435/320.1, 419, 468, 471, 252.3

(56) References Cited

U.S. PATENT DOCUMENTS

| | | | |
|---|---|---|---|
| 5,668,292 A | 9/1997 | Somerville et al. | ......... 800/205 |
| 5,801,026 A | 9/1998 | Somerville et al. | |
| 6,028,248 A | 2/2000 | Somerville et al. | |

OTHER PUBLICATIONS

Puissant et al., Biotechiques 1990 8:148.
Bligh and Dyer (1959) Can J Biochem Physiol 31:911.
Bouchez et al. (1993) Acad. Sci. Ser. Iii 316: 1188.
Ellis, JG et al. (1993) Plant J:433–43.
Broun et al. (1997) Accumulation of ricinoleic, lesquerolic, and densipolic acids in seeds of transgenic Arabidopsis plants that express a fatty acyl hydroxylase cDNA from castor bean. Plant Physiol. 113: 933–942.
Browse and Somerville (1991) The genetics of plant lipids. Biochim Biophys Acta 1082(1): 1–26.
Engeseth, N et al. (1996) Desaturation of oxygenated fatty acids in *Lesquerella* and other oil seeds. Planta 198: 238–245.
Howling et al. (1972) The specificity of fatty acid desaturases and hydroxylases. The dehydrogenation and hydroxylation of monoenoic acids. Biochim Biophys Acta, 260: 10–19.
Maeng, CY et al. (2001) Purification and Structural Analysis of the Hepatitis B Virus PreS1 Expressed from *Escherichia coli*. Biochem Biophys Res Commun: 282(3):787–92.
Ohlrogge, J (1994) Design of New Plant Products: Engineering of Fatty Acid Metabolism. Plant Physiol. 104:821–26.
Ohlrogge et al. (1991) The genetics of plant lipids. Biochim Biophys Acta 1082(1): 1–26.
Schmidt et al. (1994) Purification and PCR–based cDNA cloning of a plastidial n–6 desaturase. Plant Molecular Biology 26: 631–642.
Smith (1970) in Progress in the Chemistry of Fats and Other Lipids, vol. 11 pt 1. (Ed: Holman, RT, Ed) p 139–177.
Sperling et al. (1995) A cytochrome–b5–containing fusion protein similar to plant acyl lipid desaturases. Eur. J. Biochem. 232: 798–805.
van de Loo et al. (1993) in Lipid Metabolism in Plants. (Ed: Moore TS Jr.; CRC Press, Boca Raton, FL.) pp 91–1.
Atsmon (1989) in Oil Crops of the World: Their Breeding and Utilization (Eds: Robbelen, G, Downey KR, and Ashri, A; McGraw Hill publishing Co, New York) pp. 438–447.

*Primary Examiner*—Elizabeth F. McElwain
(74) *Attorney, Agent, or Firm*—Margaret C. Bogosian

(57) ABSTRACT

The present invention relates to oleate hydroxylase genes, proteins, and methods of their use. The present invention also relates to methods of using the oleate hydroxylase genes and proteins, including in their expression in transgenic organisms and in the production of hydroxylated fatty acids.

23 Claims, 2 Drawing Sheets

FIG. 1

```
  1 ATG GGA GGT GGT GGT CGC ATG TCT ACT GTC ATA ACC AGC AAC AAC AGT    48
  1  M   G   G   G   G   R   M   S   T   V   I   T   S   N   N   S    16

49 GAG AAG AAA GGA GGA AGC AGC CAC CTT AAG CGA GCG CCG CAC ACG AAG    96
 17  E   K   K   G   G   S   S   H   L   K   R   A   P   H   T   K    32

97 CCT CCT TTC ACA CTT GGT GAC CTC AAG AGA GCC ATC CCA CCC CAT TGC   144
 33  P   P   F   T   L   G   D   L   K   R   A   I   P   P   H   C    48

145 TTT GAA CGC TCT TTT GTG CGC TCA TTC TCC TAT GTT GCC TAT GAT GTC   192
 49  F   E   R   S   F   V   R   S   F   S   Y   V   A   Y   D   V    64

193 TGC TTA AGT TTT CTT TTC TAC TCG ATC GCC ACC AAC TTC TTC CCT TAC   240
 65  C   L   S   F   L   F   Y   S   I   A   T   N   F   F   P   Y    80

241 ATC TCT TCT CCG CTC TCG TAT GTC GCT TGG CTG GTT TAC TGG CTC TTC   288
 81  I   S   S   P   L   S   Y   V   A   W   L   V   Y   W   L   F    96

289 CAA GGC TGC ATT CTC ACT GGT CTT TGG GTC ATC GGC CAT GAA TGT GGC   336
 97  Q   G   C   I   L   T   G   L   W   V   I   G   H   E   C   G   112

337 CAT CAT GCT TTT AGT GAG TAT CAG CTG GCT GAT GAC ATT GTT GGC CTA   384
113  H   H   A   F   S   E   Y   Q   L   A   D   D   I   V   G   L   128

385 ATT GTC CAT TCT GCA CTT CTG GTT CCA TAT TTT TCA TGG AAA TAT AGC   432
129  I   V   H   S   A   L   L   V   P   Y   F   S   W   K   Y   S   144

433 CAT CGC CGC CAC CAT TCT AAC ATA GGA TCT CTC GAG CGA GAC GAA GTG   480
145  H   R   R   H   H   S   N   I   G   S   L   E   R   D   E   V   160

481 TTC GTC CCG AAA TCA AAG TCG AAA ATT TCA TGG TAT TCT AAG TAC TTA   528
161  F   V   P   K   S   K   S   K   I   S   W   Y   S   K   Y   L   176

529 AAC AAC CCG CCA GGT CGA GTT TTG ACA CTT GCT GCC ACG CTC CTC CTT   576
177  N   N   P   P   G   R   V   L   T   L   A   A   T   L   L   L   192

577 GGC TGG CCT TTA TAC TTA GCT TTC AAT GTC TCT GGT AGA CCT TAC GAT   624
193  G   W   P   L   Y   L   A   F   N   V   S   G   R   P   Y   D   208

625 CGC TTT GCT TGC CAT TAT GAT CCC TAT GGC CCA ATA TTT TCC GAA AGA   672
209  R   F   A   C   H   Y   D   P   Y   G   P   I   F   S   E   R   224
```

FIG. 1 continued

```
 673  GAA AGG CTT CAG ATT TAC ATT GCT GAC CTC GGA ATC TTT GCC ACA ACG   720
 225   E   R   L   Q   I   Y   I   A   D   L   G   I   F   A   T   T   240

721  TTT GTG CTT TAT CAG GCT ACA ATG GCA AAA GGG TTG GCT TGG GTA ATG   768
 241   F   V   L   Y   Q   A   T   M   A   K   G   L   A   W   V   M   256

769  CGT ATC TAT GGG GTG CCA TTG CTT ATT GTT AAC TGT TTC CTT GTT ATG   816
 257   R   I   Y   G   V   P   L   L   I   V   N   C   F   L   V   M   272

817  ATC ACA TAC TTG CAG CAC ACT CAC CCA GCT ATT CCA CGC TAT GGC TCA   864
 273   I   T   Y   L   Q   H   T   H   P   A   I   P   R   Y   G   S   288

865  TCG GAA TGG GAT TGG CTC CGG GGA GCA ATG GTG ACT GTC GAT AGA GAT   912
 289   S   E   W   D   W   L   R   G   A   M   V   T   V   D   R   D   304

913  TAT GGG GTG TTG AAT AAA GTA TTC CAT AAC ATT GCA GAC ACT CAT GTA   960
 305   Y   G   V   L   N   K   V   F   H   N   I   A   D   T   H   V   320

961  GCT CAT CAT CTC TTT GCT ACA GTG CCA CAT TAC CAT GCA ATG GAG GCC  1008
 321   A   H   H   L   F   A   T   V   P   H   Y   H   A   M   E   A   336

1009  ACT AAA GCA ATC AAG CCT ATA ATG GGT GAG TAT TAC CGG TAT GAT GGT  1056
 337   T   K   A   I   K   P   I   M   G   E   Y   Y   R   Y   D   G   352

1057  ACC CCA TTT TAC AAG GCA TTG TGG AGG GAG GCA AAG GAG TGC TTG TTC  1104
 353   T   P   F   Y   K   A   L   W   R   E   A   K   E   C   L   F   368

1105  GTC GAG CCA GAT GAA GGA GCT CCT ACA CAA GGC GTT TTC TGG TAC CGG  1152
 369   V   E   P   D   E   G   A   P   T   Q   G   V   F   W   Y   R   384

1153  AAC AAG TAT TAA                                                  1164
 385   N   K   Y   *                                                    388
```

ISOFORM OF CASTOR OLEATE HYDROXYLASE

This application claims priority from provisional application Ser. No. 60/302,801, filed Jun. 29, 2001, which is hereby incorporated by reference in its entirety.

This invention was made at least in part with Government support under contract number DE-AC02-98CH10886, awarded by the U.S. Department of Energy. The Government may have certain rights in the invention.

FIELD OF THE INVENTION

The present invention concerns the identification of nucleic acid sequences and constructs, and methods related thereto, and the use of these sequences and constructs to produce genetically modified plants for the purpose of altering the composition of plant oils, waxes and related compounds.

BACKGROUND

Plants have the ability to produce a diverse range of structures, including more than 20,000 different terpenoids, flavonoids, alkaloids, and fatty acids. Fatty acids have been extensively exploited for industrial uses in products such as lubricants, plasticizers, and surfactants. In fact, approximately one-third of vegetable oils produced in the world are already used for non-food purposes (Ohlrogge, J (1994) Plant Physiol. 104:821–26).

Most plant fatty acids are obtained from seed oils, which consists primarily of storage oil in the form of triglycerols, with minority contributions primarily from membrane lipids, which are predominantly phospholipids. Seed oils from different species of higher plants contain a total of more than 210 naturally occurring fatty acids, which differ by the number and arrangement of double or triple bonds and various functional groups, such as hydroxyls, ketones, epoxys, cyclopentenyl or cyclopropyl groups, furans or halogens (van de Loo et al. (1993) in Lipid Metabolism in Plants. (Ed: Moore T S Jr.; CRC Press, Boca Raton, Fla.) pp 91–126). These include at least 33 structurally distinct monohydroxylated plant fatty acids, and 12 different polyhydroxylated fatty acids have been described (reviewed by van de Loo et al. (1993) in Lipid Metabolism in Plants. (Ed: Moore T S Jr.; CRC Press, Boca Raton, Fla.) pp 91–126; Smith (1970) in Progress in the Chemistry of Fats and Other Lipids, Vol. 11 pt 1. (Ed: Holman, RT, Ed) p 139–177).

The most commonly occurring fatty acids in both membrane and storage lipids are 16- and 18-carbon fatty acids which may have from zero to three, methylene-interrupted, unsaturations. These are synthesized from the fully saturated species as the result of a series of sequential desaturations which usually begin at the DELTA 9 carbon and progress in the direction of the methyl carbon (Browse and Somerville (1991) Biochim Biophys Acta 1082(1): 1–26). Fatty acids which cannot be described by this simple algorithm are generally considered "unusual" even though several, such as lauric (12:0), erucic (22:1) and ricinoleic acid (12D-hydroxyoctadec-cis-9-enoic acid) are of significant commercial importance. The present invention is directed to the biosynthesis of hydroxylated fatty acids, such as ricinoleic acid in castor (*Ricinus communis*) seed.

Ricinoleic acid is synthesized by oleate-12-hydroxylase. A gene for this enzyme has been isolated from castor bean endosperm and sequenced (U.S. Pat. Nos. 6,028,248, 5,801, 026, and 5,668,292). However, an enzymatic activity within a species frequently exists in different variant forms, such as isoenzymes or isoforms. Isoenzymes often possess different properties, such as tissue-specific distribution or differential distribution in different cellular compartments. Isoenzymes typically have the same general catalytic activity, but differ in physical properties, such as, optimum pH, isoelectric point and stability under differing in vitro or in vivo conditions. Different isoenzymes may also demonstrate differing characteristics in transgenic organisms, making them more or less effective for a specific purpose. Therefore, it is useful to isolate different isoforms of known enzymes, such as oleate-12-hydroxylase.

SUMMARY OF THE INVENTION

It is an object of the present invention to provide a composition comprising at least one isoform of castor bean oleate-12-hydroxylase, and nucleic acids encoding the same. It is a further object of the present invention to provide methods of using the isoform of 12-oleate-hydroxylase to modify seed oils.

The present invention provides an isolated nucleic acid sequence comprising SEQ ID NO:1 or encoding SEQ ID NO: 2; the present invention also provides a purified protein comprising SEQ ID NO: 2. In one embodiment, the present invention further provides compositions comprising a recombinant DNA molecule comprising SEQ ID NO. 1, or a nucleic acid sequence encoding SEQ ID NO: 2, which is operably linked to at least one suitable regulatory sequence. The present invention further provides an expression vector comprising a recombinant DNA molecule comprising SEQ ID NO. 1, or a nucleic acid sequence encoding SEQ ID NO: 2, which is operably linked to at least one suitable regulatory sequence.

The present invention also provides an organism transformed with the recombinant DNA molecule comprising SEQ ID NO. 1, or a nucleic acid sequence encoding SEQ ID NO: 2, operably linked to at least one suitable regulatory sequence; preferably, the organism is selected from the group consisting of microorganisms and plants; even more preferably, the organism is a plant; most preferably, the plant is selected from the group consisting of soybean (*Glycine max*), rapeseed and canola (including *Brassica napus* and *B. cainpestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*) and peanut (*Arachis hypogaea*). The present invention also provides a plant cell or a plant seed transformed with the recombinant DNA molecule comprising SEQ ID NO. 1, or a nucleic acid sequence encoding SEQ ID NO: 2, operably linked to at least one suitable regulatory sequence.

The present invention also provides a method of producing a plant hydroxylase in a transgenic organism, comprising providing an organism transformed with the recombinant DNA molecule comprising SEQ ID NO. 1, or a nucleic acid sequence encoding SEQ ID NO: 2, operably linked to at least one suitable regulatory sequence; growing the organism under conditions such that a hydroxylase encoded by SEQ ID NO: 1, or a nucleic acid sequence encoding SEQ ID NO: 2, is expressed. Preferably, the organism is a plant. In one aspect, the recombinant DNA molecule is integrated into the genome of the plant. The present invention also provides a plant hydroxylase according to claim 20.

The present invention further provides methods for altering the phenotype of a plant comprising: providing a vector comprising SEQ ID NO: 1 or comprising a nucleic acid sequence encoding SEQ ID NO: 2, and a plant; and transfecting the plant with the vector under conditions such that the protein is expressed.

The present invention also provides methods to alter the phenotype of a plant comprising: providing a vector comprising an antisense sequence corresponding SEQ ID NO: 1, or to a nucleic acid sequence encoding SEQ ID NO: 2, and a plant; and transfecting the plant with the vector under conditions such that the antisense sequence is expressed and wherein the activity of an oleate hydroxylase is down-regulated as compared to wild-type plants.

DESCRIPTION OF THE FIGURES

FIG. 1 shows a nucleic acid sequence encoding the oleate hydroxylase of the present invention (SEQ ID NO: 1), and the amino acid sequence of the oleate hydroxylase of the present invention (SEQ ID NO: 2).

DEFINITIONS

To facilitate an understanding of the present invention, a number of terms and phrases as used herein are defined below:

The term "microorganism" is used in its broadest sense. It includes, but is not limited to, microscopic organisms (and taxonomically related macroscopic organisms) within the categories algae, bacteria, fungi (including lichens), protozoa, viruses, and subviral agents.

The term "plant" is used in its broadest sense. It includes, but is not limited to, any species of woody, ornamental or decorative, crop or cereal, fruit or vegetable plant, and photosynthetic green algae (for example, (Chlamydomonas reinhardtii). It also refers to a plurality of plant cells which are largely differentiated into a structure that is present at any stage of a plant's development. Such structures include, but are not limited to, a fruit, shoot, stem, leaf, flower petal, etc. The term "plant tissue" includes differentiated and undifferentiated tissues of plants including those present in roots, shoots, leaves, pollen, seeds and tumors, as well as cells in culture (for example, single cells, protoplasts, embryos, callus, etc.). Plant tissue may be in planta, in organ culture, tissue culture, or cell culture. The term "plant part" as used herein refers to a plant structure or a plant tissue.

The term "crop" or "crop plant" is used in its broadest sense. The term includes, but is not limited to, any species of plant or algae edible by humans or used as a feed for animals or used, or consumed by humans, or any plant or algae used in industry or commerce.

The term "oil-producing species" refers to plant species which produce and store triacylglycerol in specific organs, primarily in seeds. Such species include but are not limited to soybean (Glycine max), rapeseed and canola (including Brassica napus and B. campestris), sunflower (Helianthus annus), cotton (Gossypium hirsutum), corn (Zea mays), cocoa (Theobroma cacao), safflower (Carthamus tinctorius), oil palm (Elaeis guineensis), coconut palm (Cocos nucifera), flax (Linum usitatissimum), castor (Ricinus communis) and peanut (Arachis hypogaea). The group also includes non-agronomic species which are useful in developing appropriate expression vectors such as tobacco, rapid cycling Brassica species, and Arabidopsis thaliana, and wild species which may be a source of unique fatty acids.

The term plant cell "compartments or organelles" is used in its broadest sense. The term includes but is not limited to, the endoplasmic reticulum, Golgi apparatus, trans Golgi network, plastids, sarcoplasmic reticulum, glyoxysomes, mitochondrial, chloroplast, and nuclear membranes, and the like.

The term "hydroxylase" refers to a monooxygenase (also mixed-function oxidase and mixed-function oxygenase), which is an oxygenase which catalyses the incorporation of one atom of molecular oxygen into a substrate molecule, the other oxygen atom being reduced to water; the reducing power need for monooxygenase activity may be supplied for example by NADH.

The term "oleate hydroxylase" refers to a sequence of amino acids, such as a protein, polypeptide or peptide fragment, which comprises SEQ ID NO: 2 and which demonstrates the ability to catalyze the production of hydroxy-oleic acid from oleic acid substrates under enzyme reactive conditions; the substrate may be free fatty acid, a fatty acid salt, oleoyl-CoA, oleoyl-ACP or an oleoyl-lipid. By "enzyme reactive conditions" is meant that any necessary conditions (in other words, such factors as temperature, pH, lack of inhibiting substances) which will permit the enzyme to function. The enzyme may also demonstrate the ability to catalyze the production of other hydroxy-fatty acids.

The terms "ricinoleate" or "ricinoleic acid" or "hydroxy-oleate" or "hydroxy-oleic acid" refer to 12D-hydroxyoctadec-cis-9-enoic acid, and include the free acids, the ACP and CoA esters, the salts of these acids, the glycerolipid esters (particularly the triacylglycerol esters), the wax esters, and the ether derivatives of these acids.

The term "chimera" or "chimeric" when used in reference to a polypeptide refers to the expression product of two or more coding sequences obtained from different genes, that have been cloned together and that, after translation, act as a single polypeptide sequence. Chimeric polypeptides are also referred to as "hybrid" polypeptides. The coding sequences includes those obtained from the same or from different species of organisms.

The term "fusion" when used in reference to a polypeptide refers to a chimeric protein containing a protein of interest joined to an exogenous protein fragment (the fusion partner). The fusion partner may serve various functions, including enhancement of solubility of the polypeptide of interest, as well as providing an "affinity tag" to allow purification of the recombinant fusion polypeptide from a host cell or from a supernatant or from both. If desired, the fusion partner may be removed from the protein of interest after or during purification.

The term "homolog" or "homologous" when used in reference to a polypeptide refers to a high degree of sequence identity between two polypeptides, or to a high degree of similarity between the three-dimensional structure or to a high degree of similarity between the active site and the mechanism of action. In a preferred embodiment, a homolog has a greater than 60% sequence identity, and more preferably greater than 75% sequence identity, and still more preferably greater than 90% sequence identity, with a reference sequence.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (for example, 99 percent sequence identity). Preferably, residue positions which are not identical differ by conservative amino acid substitutions.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (for example, replacement of a glycine with a tryptophan). Similar minor variations may also include amino acid deletions or insertions (in other words, additions), or both.

The term "gene" refers to a nucleic acid (for example, DNA or RNA) sequence that comprises coding sequences necessary for the production of an RNA, or a polypeptide or its precursor (for example, proinsulin). A functional polypeptide can be encoded by a full length coding sequence or by any portion of the coding sequence as long as the desired activity or functional properties (for example, enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

The term "heterologous" when used in reference to a gene refers to a gene encoding a factor that is not in its natural environment (in other words, has been altered by the hand of man). For example, a heterologous gene includes a gene from one species introduced into another species. A heterologous gene also includes a gene native to an organism that has been altered in some way (for example, mutated, added in multiple copies, linked to a non-native promoter or enhancer sequence, etc.). Heterologous genes may comprise plant gene sequences that comprise cDNA forms of a plant gene; the cDNA sequences may be expressed in either a sense (to produce mRNA) or anti-sense orientation (to produce an anti-sense RNA transcript that is complementary to the mRNA transcript). Heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (for example, genes expressed in loci where the gene is not normally expressed).

The term "nucleotide sequence of interest" or "nucleic acid sequence of interest" refer to any nucleotide sequence (for example, RNA or DNA) the manipulation of which may be deemed desirable for any reason (for example, treat disease, confer improved qualities, etc.), by one of ordinary skill in the art. Such nucleotide sequences include, but are not limited to, coding sequences of structural genes (for example, reporter genes, selection marker genes, oncogenes, drug resistance genes, growth factors, etc.), and non-coding regulatory sequences which do not encode an mRNA or protein product (for example, promoter sequence, polyadenylation sequence, termination sequence, enhancer sequence, etc.).

The term "structural" when used in reference to a gene or to a nucleotide or nucleic acid sequence refers to a gene or a nucleotide or nucleic acid sequence whose ultimate expression product is a protein (such as an enzyme or a structural protein), an rRNA, an sRNA, a tRNA, etc.

The term "oligonucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

The term "an oligonucleotide having a nucleotide sequence encoding a gene" or "a nucleic acid sequence encoding" a specified polypeptide refers to a nucleic acid sequence comprising the coding region of a gene or in other words the nucleic acid sequence which encodes a gene product. The coding region may be present in either a cDNA, genomic DNA or RNA form. When present in a DNA form, the oligonucleotide may be single-stranded (in other words, the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "complementary" and "complementarity" refer to polynucleotides (in other words, a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" when used in relation to nucleic acids refers to a degree of complementarity. There may be partial homology or complete homology (in other words, identity). "Sequence identity" refers to a measure of relatedness between two or more nucleic acids or proteins, and is given as a percentage with reference to the total comparison length. The identity calculation takes into account those nucleotide or amino acid residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence is one that at least partially inhibits (or competes with) a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (in other words, the hybridization) of a sequence which is completely homologous to a target under conditions of low stringency. This is not to say that conditions of low stringency are such that non-specific binding is permitted; low stringency conditions require that the binding of two sequences to one another be a specific (in other words, selective) interaction. The absence of non-specific binding may be tested by the use of a second target which lacks even a partial degree of complementarity (for example, less than about 30% identity); in the absence of non-specific binding the probe will not hybridize to the second non-complementary target.

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (in other words, a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (in other words, gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Smith and Waterman (1981) Adv. Appl. Math. 2: 482) by the homology alignment algorithm of Needleman and Wunsch (Needleman and Wunsch (1970) J. Mol. Biol. 48:443), by the search for similarity method of Pearson and Lipman (Pearson and Lipman (1988) Proc. Natl. Acad. Sci. (U.S.A.) 85:2444), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (in other words, resulting in the highest percentage of homology over the comparison window) generated by the various methods is selected. The term "sequence identity" means that two polynucleotide sequences are identical (in other words, on a nucleotide-by-nucleotide basis) over the window of comparison. The term "percentage of sequence identity" is calculated by comparing two optimally aligned sequences over the window of comparison, determining the number of positions at which the identical nucleic acid base (for example, A, T, C, G, U, or I) occurs in both sequences to yield the number of matched positions, dividing the number of matched positions by the total number of positions in the window of comparison (in other words, the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison.

The term "substantially homologous" when used in reference to a double-stranded nucleic acid sequence such as a cDNA or genomic clone refers to any probe that can hybridize to either or both strands of the double-stranded nucleic acid sequence under conditions of low to high stringency as described above.

The term "substantially homologous" when used in reference to a single-stranded nucleic acid sequence refers to any probe that can hybridize (in other words, it is the complement of) the single-stranded nucleic acid sequence under conditions of low to high stringency as described above.

The term "hybridization" refers to the pairing of complementary nucleic acids. Hybridization and the strength of hybridization (in other words, the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

The term "$T_m$" refers to the "melting temperature" of a nucleic acid. The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41$ (% G+C), when a nucleic acid is in aqueous solution at 1 M NaCl (See for example, Anderson and Young (1985) Quantitative Filter Hybridization, in *Nucleic Acid Hybridization*). Other references include more sophisticated computations that take structural as well as sequence characteristics into account for the calculation of $T_m$.

The term "stringency" refers to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less.

"Low stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$●H$_2$O and 1.85 g/l EDTA, pH adjusted to 7.4 with NaOH), 0.1% SDS, 5× Denhardt's reagent (50× Denhardt's contains per 500 ml: 5 g Ficoll (Type 400, Pharmacia), 5 g BSA (Fraction V; Sigma)) and 100 μg/ml denatured salmon sperm DNA followed by washing in a solution comprising 5×SSPE, 0.1% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$●H$_2$O and 1.85 g/l EDTA, pH adjusted to 7.4 with NaOH), 0.5% SDS, 5× Denhardt's reagent and 100 μg/ml denatured salmon sperm DNA followed by washing in a solution comprising 1.0× SSPE, 1.0% SDS at 42° C. when a probe of about 500 nucleotides in length is employed.

"High stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$●H$_2$O and 1.85 g/l EDTA, pH adjusted to 7.4 with NaOH), 0.5% SDS, 5× Denhardt's reagent and 100 μg/ml denatured salmon sperm DNA followed by washing in a solution comprising 0.1× SSPE, 1.0% SDS at 42° C. when a probe of about 500 nucleotides in length is employed.

It is well known that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (for example, the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (for example, increasing the temperature of the hybridization and/or wash steps, the use of formamide in the hybridization solution, etc.).

The term "amplification" refers to a special case of nucleic acid replication involving template specificity. It is to be contrasted with non-specific template replication (in other words, replication that is template-dependent but not dependent on a specific template). Template specificity is here distinguished from fidelity of replication (in other words, synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q_replicase, MDV-1 RNA is the specific template for the replicase (Kacian et al. (1972) Proc. Natl. Acad. Sci. USA, 69:3038). Other nucleic acid will not be replicated by this amplification enzyme. Similarly, in the case of T7 RNA polymerase, this amplification enzyme has a stringent specificity for its own promoters (Chamberlin et al. (1970) Nature: 228:227). In the case of T4 DNA ligase, the enzyme will not ligate the two oligonucleotides or polynucleotides, where there is a mismatch between the oligonucleotide or polynucleotide substrate and the template at the ligation junction (Wu and Wallace (1989) Genomics: 4:560). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), *PCR Technology*, Stockton Press (1989)).

The term "amplifiable nucleic acid" refers to nucleic acids that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (in other words, in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The term "probe" refers to an oligonucleotide (in other words, a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (for example, ELISA, as well as enzyme-based histochemical assays), fluorescent, radioactive, and luminescent systems. It is not intended that the present invention be limited to any particular detection system or label.

The term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (in other words, denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (for example, hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

The terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

The term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

The term "reverse-transcriptase" or "RT-PCR" refers to a type of PCR where the starting material is mRNA. The starting mRNA is enzymatically converted to complementary DNA or "cDNA" using a reverse transcriptase enzyme. The cDNA is then used as a "template" for a "PCR" reaction.

The term "gene expression" refers to the process of converting genetic information encoded in a gene into RNA (for example, mRNA, rRNA, tRNA, or snRNA) through "transcription" of the gene (in other words, via the enzymatic action of an RNA polymerase), and into protein, through "translation" of mRNA. Gene expression can be regulated at many stages in the process. "Up-regulation" or "activation" refers to regulation that increases the production of gene expression products (in other words, RNA or protein), while "down-regulation" or "repression" refers to regulation that decrease production. Molecules (for example, transcription factors) that are involved in up-regulation or down-regulation are often called "activators" and "repressors," respectively.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis, et al. (1987) Science 236:1237). Promoter and enhancer elements have been isolated from a variety of eukaryotic sources including genes in yeast, insect, mammalian and plant cells. Promoter and enhancer elements have also been isolated from viruses and analogous control elements such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., (1986) Trends Biochem. Sci., 11:287 and Maniatis, et al., (1987) supra).

The terms "promoter element," "promoter," or "promoter sequence" refer to a DNA sequence that is located at the 5' end (in other words precedes) of the coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

The term "regulatory region" refers to a gene's 5' transcribed but untranslated regions, located immediately downstream from the promoter and ending just prior to the translational start of the gene.

The term "promoter region" refers to the region immediately upstream of the coding region of a DNA polymer, and is typically between about 500 bp and 4 kb in length, and is preferably about 1 to 1.5 kb in length.

Promoters may be tissue specific or cell specific. The term "tissue specific" as it applies to a promoter refers to a promoter that is capable of directing selective expression of a nucleotide sequence of interest to a specific type of tissue (for example, seeds) in the relative absence of expression of the same nucleotide sequence of interest in a different type of tissue (for example, leaves). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (for example, detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, for example, immunohistochemical staining. Briefly, tissue sections are embedded in paraffin, and paraffin sections are reacted with a primary antibody which is specific for the polypeptide product encoded by the nucleotide sequence of interest whose expression is controlled by the promoter. A labeled (for example, peroxidase conjugated) secondary antibody which is specific for the primary antibody is allowed to bind to the sectioned tissue and specific binding detected (for example, with avidin/biotin) by microscopy.

Promoters may be constitutive or inducible. The term "constitutive" when made in reference to a promoter means that the promoter is capable of directing transcription of an operably linked nucleic acid sequence in the absence of a stimulus (for example, heat shock, chemicals, light, etc.). Typically, constitutive promoters are capable of directing expression of a transgene in substantially any cell and any tissue. Exemplary constitutive plant promoters include, but are not limited to SD Cauliflower Mosaic Virus (CaMV SD; see for example, U.S. Pat. No. 5,352,605, incorporated herein by reference), mannopine synthase, octopine synthase (ocs), superpromoter (see for example, WO 95/14098), and ubi3 (see for example, Garbarino and Belknap (1994) Plant Mol. Biol. 24:119–127) promoters. Such promoters have been used successfully to direct the expression of heterologous nucleic acid sequences in transformed plant tissue.

In contrast, an "inducible" promoter is one which is capable of directing a level of transcription of an operably linked nucleic acid sequence in the presence of a stimulus (for example, heat shock, chemicals, light, etc.) which is different from the level of transcription of the operably linked nucleic acid sequence in the absence of the stimulus.

The term "regulatory element" refers to a genetic element that controls some aspect of the expression of nucleic acid sequence(s). For example, a promoter is a regulatory element that facilitates the initiation of transcription of an operably linked coding region. Other regulatory elements are splicing signals, polyadenylation signals, termination signals, etc.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (in other words, molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (for example, the first and second genes can be from the same species, or from different species).

The term "naturally linked" or "naturally located" when used in reference to the relative positions of nucleic acid sequences means that the nucleic acid sequences exist in nature in the relative positions.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al. *Molecular Cloning: A Laboratory Manual*, 2nd ed., Cold Spring Harbor Laboratory Press, New York (1989) pp. 16.7–16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly(A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly (A) signal. The SV40 poly(A) signal is contained on a 237 bp BamHI/BclI restriction fragment and directs both termination and polyadenylation (Sambrook, supra, at 16.6–16.7).

The term "vector" refers to nucleic acid molecules that transfer DNA segment(s) from one cell to another. The term "vehicle" is sometimes used interchangeably with "vector."

The terms "expression vector" or "expression cassette" refer to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The term "transfection" refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (in other words, particle bombardment) and the like.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, 1973, Virol., 52:456), has been modified by several groups to optimize conditions for particular types of cells. The art is well aware of these numerous modifications.

The terms "infecting" and "infection" when used with a bacterium refer to co-incubation of a target biological sample, (for example, cell, tissue, etc.) with the bacterium under conditions such that nucleic acid sequences contained within the bacterium are introduced into one or more cells of the target biological sample.

The term "Agrobacterium" refers to a soil-borne, Gram-negative, rod-shaped phytopathogenic bacterium which causes crown gall. The term "Agrobacterium" includes, but is not limited to, the strains Agrobacterium tumefaciens, (which typically causes crown gall in infected plants), and Agrobacterium rhizogens (which causes hairy root disease in infected host plants). Infection of a plant cell with Agrobacterium generally results in the production of opines (for example, nopaline, agropine, octopine etc.) by the infected cell. Thus, Agrobacterium strains which cause production of nopaline (for example, strain LBA4301, C58, A208, GV3101) are referred to as "nopaline-type" Agrobacteria; Agrobacterium strains which cause production of octopine (for example, strain LBA4404, Ach5, B6) are referred to as "octopine-type" Agrobacteria; and Agrobacterium strains which cause production of agropine (for example, strain EHA105, EHA101, A281) are referred to as "agropine-type" Agrobacteria.

The terms "bombarding, "bombardment," and "biolistic bombardment" refer to the process of accelerating particles towards a target biological sample (for example, cell, tissue, etc.) to effect wounding of the cell membrane of a cell in the target biological sample and/or entry of the particles into the target biological sample. Methods for biolistic bombardment are known in the art (for example, U.S. Pat. No. 5,584,807, the contents of which are incorporated herein by reference), and are commercially available (for example, the helium gas-driven microprojectile accelerator (PDS-1000/He, BioRad).

The term "microwounding" when made in reference to plant tissue refers to the introduction of microscopic wounds in that tissue. Microwounding may be achieved by, for example, particle bombardment as described herein.

The term "transgene" refers to a foreign gene that is placed into an organism by the process of transfection. The term "foreign gene" refers to any nucleic acid (for example, gene sequence) that is introduced into the genome of an organism by experimental manipulations and may include gene sequences found in that organism so long as the introduced gene does not reside in the same location as does the naturally-occurring gene.

The term "transgenic" when used in reference to a plant or fruit or seed (in other words, a "transgenic plant" or "transgenic fruit" or a "transgenic seed") refers to a plant or fruit or seed that contains at least one heterologous or foreign gene in one or more of its cells. The term "transgenic plant material" refers broadly to a plant, a plant structure, a plant tissue, a plant seed or a plant cell that contains at least one heterologous gene in one or more of its cells.

The term "host cell" refers to any cell capable of replicating and/or transcribing and/or translating a heterologous gene. Thus, a "host cell" refers to any eukaryotic or prokaryotic cell (for example, bacterial cells such as E. coli, yeast cells, mammalian cells, avian cells, amphibian cells, plant cells, fish cells, and insect cells), whether located in vitro or in vivo. For example, host cells may be located in a transgenic animal.

The terms "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term "selectable marker" refers to a gene which encodes an enzyme having an activity that confers resistance to an antibiotic or drug upon the cell in which the selectable marker is expressed, or which confers expression of a trait which can be detected (for example., luminescence or fluorescence). Selectable markers may be "positive" or "negative." Examples of positive selectable markers include the neomycin phosphotrasferase (NPTII) gene which confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The term "reporter gene" refers to a gene encoding a protein that may be assayed. Examples of reporter genes include, but are not limited to, luciferase (See, for example, deWet et al. (1987) Mol. Cell. Biol. 7:725 and U.S. Pat Nos. 6,074,859; 5,976,796; 5,674,713; and 5,618,682; all of which are incorporated herein by reference), green fluorescent protein (for example, GenBank Accession Number U43284; a number of GFP variants are commercially available from CLONTECH Laboratories. Palo Alto, Calif.), chloramphenicol acetyltransferase, β-galactosidase, alkaline phosphatase, and horse radish peroxidase.

The term "wild-type" when made in reference to a gene refers to a gene which has the characteristics of a gene isolated from a naturally occurring source. The term "wild-type" when made in reference to a gene product refers to a gene product which has the characteristics of a gene product isolated from a naturally occurring source. The term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. A wild-type gene is that which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (in other words, altered characteristics) when compared to the wild-type gene or gene product. It is noted that naturally-occurring mutants can be isolated; these are identified by the fact that they have altered characteristics when compared to the wild-type gene or gene product.

The term "antisense" refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex which is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, in other words, at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target protein.

The term "overexpression" generally refers to the production of a gene product in transgenic organisms that exceeds levels of production in normal or non-transformed organisms. The term "cosuppression" refers to the expression of a foreign gene which has substantial homology to an endogenous gene resulting in the suppression of expression of both the foreign and the endogenous gene. As used herein, the term "altered levels" refers to the production of gene product(s) in transgenic organisms in amounts or proportions that differ from that of normal or non-transformed organisms.

The terms "overexpression" and "overexpressing" and grammatical equivalents, are used specifically in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis (See, Example 10, for a protocol for performing Northern blot analysis). Appropriate controls are included on the Northern blot to control for differences in the amount of RNA loaded from each tissue analyzed (for example, the amount of 28S rRNA, an abundant RNA transcript present at essentially the same amount in all tissues, present in each sample can be used as a means of normalizing or standardizing the RAD50 mRNA-specific signal observed on Northern blots).

The terms "Southern blot analysis" and "Southern blot" and "Southern" refer to the analysis of DNA on agarose or acrylamide gels in which DNA is separated or fragmented according to size followed by transfer of the DNA from the gel to a solid support, such as nitrocellulose or a nylon membrane. The immobilized DNA is then exposed to a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., Molecular Cloning. A Laboratory Manual, Cold Spring Harbor Press, NY (1989), pp 9.31–9.58).

The terms "Northern blot analysis" and "Northern blot" and "Northern" refer to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al. supra, pp 7.39–7.52).

The terms "Western blot analysis" and "Western blot" and "Western" refers to the analysis of protein(s) (or polypeptides) immobilized onto a support such as nitrocellulose or a membrane. A mixture comprising at least one protein is first separated on an acrylamide gel, and the separated proteins are then transferred from the gel to a solid support, such as nitrocellulose or a nylon membrane. The immobilized proteins are exposed to at least one antibody with reactivity against at least one antigen of interest. The bound antibodies may be detected by various methods, including the use of radiolabeled antibodies.

The term "antigenic determinant" refers to that portion of an antigen that makes contact with a particular antibody (in other words, an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (in other words, the "immunogen" used to elicit the immune response) for binding to an antibody.

The terms "protein" and "polypeptide" refer to compounds comprising amino acids joined via peptide bonds and are used interchangeably. A "protein" or "polypeptide" encoded by a gene is not limited to the amino acid sequence encoded by the gene, but includes post-translational modifications of the protein.

Where the term "amino acid sequence" is recited herein to refer to an amino acid sequence of a protein molecule, an "amino acid sequence" can be deduced from the nucleic acid sequence encoding the protein.

The term "portion" when used in reference to a protein (as in "a portion of a given protein") refers to fragments of that protein. The fragments may range in size from four amino acid residues to the entire amino sequence minus one amino acid.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. For example, a given DNA sequence (for example, a gene) is found on the host cell chromosome in proximity to neighboring genes; RNA sequences, such as a specific mRNA sequence encoding a specific protein, are found in the cell as a mixture with numerous other mRNA s which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (in other words, the oligonucleotide may single-stranded), but may contain both the sense and anti-sense strands (in other words, the oligonucleotide may be double-stranded).

The term "purified" refers to molecules, either nucleic or amino acid sequences, that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated. As used herein, the term "purified" or "to purify" also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "sample" is used in its broadest sense. In one sense it can refer to a plant cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

GENERAL DESCRIPTION OF THE INVENTION

Castor (*Ricinus communis* L.) is a minor oilseed crop. Approximately 50% of the seed weight is oil (triacylglycerol) in which 85–90% of total fatty acids are the hydroxylated fatty acid, ricinoleic acid (12D-hydroxyoctadec-cis-9-enoic acid). Oil pressed or extracted from castor seeds has many industrial uses based upon the properties endowed by the hydroxylated fatty acid. The most important uses are production of paints and varnishes, nylon-type synthetic polymers, resins, lubricants, and cosmetics (Atsmon (1989) in Oil Crops of the World: Their Breeding and Utilization (Eds: Robbelen, G, Downey K R, and Ashri, A; McGraw Hill publishing Co, New York) pp.438–447). In addition to oil, the castor seed contains the extremely toxic protein ricin, allergenic proteins, and the alkaloid ricinine. These constituents preclude the use of the untreated seed meal (following oil extraction) as a livestock feed, normally an important economic aspect of oilseed utilization. Furthermore, with the variable nature of castor plants and a lack of investment in breeding, castor has few favorable agronomic characteristics. For a combination of these reasons, castor is no longer grown in the United States and the development of an alternative domestic source of hydroxylated fatty acids would be attractive. The production of ricinoleic acid, the important constituent of castor oil, in an established oilseed crop through genetic engineering would be a particularly effective means of creating a domestic source.

The biosynthesis of ricinoleic acid from oleic acid in the developing endosperm of castor has been studied by a variety of methods. Data from a study of the substrate specificity of the hydroxylase show that all substrate parameters (in other words chain length and double bond position with respect to both ends) are important; deviations in these parameters caused reduced activity relative to oleic acid (Howling et al. (1972) Biochim Biophys Acta, 260: 10–16). The position at which the hydroxyl was introduced, however, was determined by the position of the double bond, being three carbons distal. Thus, the castor acyl hydroxylase enzyme can produce a family of different hydroxylated fatty acids depending on the availability of substrates. Therefore, although the enzyme is referred herein as oleate hydroxylase, it can more properly be considered an acyl hydroxylase of broad substrate specificity.

The presently claimed invention provides compositions comprising an isolated oleate hydroxylase gene and polypeptide, and in particular to compositions comprising an isolated oleate hydroxylase gene comprising SEQ ID NO: 1 or encoding a polypeptide comprising the amino acid sequence shown in SEQ ID NO: 2, and to a purified oleate hydroxylase protein comprising SEQ ID NO: 2. The encoded enzyme of the claimed invention is a previously undescribed isoform of oleate hydroxylase. When compared to a coding sequence for this enzyme which was previously isolated from castor bean endosperm and sequenced (U.S. Pat. Nos. 6,028,248, 5,801,026, and 5,668,292), it was discovered that the enzyme of the present invention carries a point mutation at codon 176 that encodes a leucine in place of the serine present in the previously described gene. The source of the seed tissue used to isolate RNA from which the novel oleate hydroxylase cDNA was identified is the same seed tissue as was used to generate the library from which the original oleate hydroxylase cDNA was isolated. Moreover, although the novel form of the hydroxylase was found in 6 independent isolates and from two independent cDNA syntheses, the previously reported sequence was not isolated in these experiments. The substitution in the novel isoform of the present invention is not conservative. Conservative amino acid substitutions are those in which a substituted amino acid has similar structural or chemical properties. One type of conservative amino acid substitutions refers to the interchangeability of residues having similar side chains. The substitution of the novel isoform is also not seen in any of the other hydroxylase or desaturase sequences of the GenBank DNA database.

Identification and isolation of a nucleic acid sequence encoding the oleate hydroxylase of the present invention is described in Example 1. The present invention also provides methods for using oleate hydroxylase genes and polypeptides; such methods include but are not limited to using the oleate hydroxylase genes and polypeptides in the production of hydroxylated fatty acids. The description below provides specific, but not limiting, illustrative examples of embodiments of the present invention.

A. Encoding Sequences and Polypeptides

1. Coding Sequences

The present invention provides an isolated nucleic acid sequence comprising SEQ ID NO: 1 or encoding a polypeptide comprising the amino acid sequence shown in SEQ ID NO: 2. The nucleic acid sequence can be oriented to produce sense or antisense transcripts, depending on the desired use In one embodiment, a nucleic acid sequence of the present invention is obtained from castor bean endosperm, as described in Example 1. In an alternative embodiment of the invention, the coding sequence for oleate hydroxylase as shown in SEQ ID NO: 2 is synthesized, whole or in part, using chemical methods well known in the art (See for example, Caruthers et al. (1980)Nucl. Acids Res. Symp. Ser., 7:215–233; Crea and Horn (1980) Nucl. Acids Res., 9:2331; Matteucci and Caruthersm (1980) Tetrahedron Lett., 21:719; and Chow and Kempe (1981) Nucl. Acids Res., 9:2807–2817).

In other aspects, the present invention provides vectors comprising a nucleic acid sequence comprising SEQ ID NO: 1 or encoding a polypeptide comprising the amino acid sequence shown in SEQ ID NO: 2. The vectors include cloning vectors and expression vectors; both types of vectors are well known in the art, and are described further below.

2. Polypeptides

The present invention also provides an oleate hydroxylase polypeptide as well as fusion proteins thereof. In some embodiments of the present invention, the polypeptide is a naturally purified product, while in other embodiments it is a product of chemical synthetic procedures, and in still other embodiments it is produced by recombinant techniques using a prokaryotic or eukaryotic host (for example, by bacterial, yeast, higher plant, insect and mammalian cells in culture). In some embodiments, depending upon the host employed in a recombinant production procedure, the polypeptide of the present invention is glycosylated or is non-glycosylated. In other embodiments, the polypeptides of the invention may also include an initial methionine amino acid residue.

An oleate hydroxylase of the present invention is a sequence of amino acids, such as a protein, polypeptide or peptide fragment, which comprises SEQ ID NO: 2 and which has the ability to catalyze the production of hydroxy-oleic acid from appropriate fatty oleoyl substrates under enzyme reactive conditions. By "enzyme reactive conditions" is meant any necessary conditions (for example, factors such as temperature, pH, lack of inhibiting substances) which will permit the enzyme to function. Appropriate enzyme reactive conditions may occur in vivo or in vitro. An appropriate oleoyl substrate may be free oleic acid, an oleic acid salt, oleoyl-CoA, oleoyl-ACP or an oleoyl-lipid. The enzyme may also demonstrate the ability to catalyze the production of other hydroxy-fatty acids, as described below.

References to fatty acid substrates and products, such as oleate or oleic acid, or ricinoleate or ricinoleic acid, are intended to include the free acids, the ACP and CoA esters, the salts of these acids, the glycerolipid esters (particularly the phospholipid and triacylglycerol esters), the wax esters, and the ether derivatives of these acids. Fatty acids are indicated by the number of carbon atoms, with the number of double bonds following an asterisk; the location of the double bond is indicated by a superscript numeral following a delta. The common name, when included, follow in parentheses. For example, a fatty acid with 18 carbon atoms and one double bond between carbons 9 and 10 (numbering from the carboxyl end) is indicated as $18:1^{\Delta 9}$ (oleate). The presence and location of a hydroxyl group is indicated by an OH following a number which indicates the carbon atom to which the hydroxyl is attached. For example, a fatty acid with 18 carbon atoms and one double bond between carbons 9 and 10 (numbering from the carboxyl end) and with a hydroxyl group at carbon 12 is indicated as 12-OH, $18:1^{\Delta 9}$ (ricinoleate).

In one aspect, it is contemplated that the oleate hydroxylase of the present invention is used for production of hydroxylated fatty acids, by expression of the enzyme either in vitro or in vivo in transgenic organisms which produce the non hydroxylated precursors, such as plants. In some embodiments, products of oleate hydroxylase include but are not limited to: 12-OH, $16:1^{\Delta 9}$; 9-OH, $18:1^{\Delta 6}$; 12-OH, $18:1^{\Delta 9}$(ricinoleate); 14-OH, $20:1^{\Delta 11}$ (lesqueroleate); and 16-OH, $22:1^{\Delta 13}$. In another aspect, it is contemplated that the oleate hydroxylase of the present invention is used for the production of additionally modified fatty acids that result from desaturation or elongation of hydroxylated fatty; such products include but are not limited to: 12-OH, $18:2^{\Delta 9,15}$ (densipoleate); 14-OH, $20:2^{\Delta 11,17}$ (aruicoleate); 14-OH, $20:1^{\Delta 11}$ (lesqueroleate); and 16-OH, $22:1^{\Delta 13}$. Substrates of the oleate hydroxylase include but are not limited to: $16:1^{\Delta 9}$ (palmitoleate); $18:1^{\Delta 6}$ (petroselenate); $18:1^{\Delta 9}$ (oleate); $20:1^{\Delta 11}$ (gladoleate or eicosenoate); and $22:1^{\Delta 13}$ (erucate or docosenoate).

An oleate hydroxylase of this invention displays activity toward fatty acyl substrates. During biosynthesis of lipids in a plant cell, fatty acids are typically covalently bound to acyl carrier protein (ACP), coenzyme A (CoA) or various cellular lipids. Thus, in various aspects, it is contemplated that the oleate hydroxylase of the present invention utilizes a fatty acyl substrate which is esterified to ACP, to CoA, or to a glycerolipid backbone. Alternatively, the fatty acid substrate is a free fatty acid. Preferably, the substrate is an esterified oleoyl substrate; most preferably, the substrate is oleoyl phosphatidylcholine.

a. Assay of Oleate Hydroxylase

Oleate hydroxylase catalyzes the following reaction:

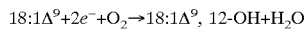

$$18:1\Delta^9 + 2e^- + O_2 \rightarrow 18:1\Delta^9, 12\text{-}OH + H_2O$$

The enzyme in situ acts on a fatty acid esterified to a lipid, and requires cytochrome $b_5$ reductase and cytochrome b5 for activity. Moreover, the enzyme may utilize different substrates under different conditions to differing degrees of activity.

The activity of oleate hydroxylase may be assayed in a number of ways. In one aspect, the activity is determined by expressing a nucleic acid sequence encoding the hydroxylase in a transgenic organism and then analyzing the composition of the total fatty acids. Thus, the activity is measured as the presence of or increase in the amount of endogenous hydroxy-oleate and other hydroxy fatty acids in a transgenic organism which comprises an exogenous nucleic acid sequence comprising SEQ ID NO: 1 or encoding a polypeptide comprising the amino acid sequence shown in SEQ ID NO: 2; such transgenic organisms are obtained as described below. The amount of hydroxy fatty acid in a transgenic organism is compared to that present in a non-transgenic organism. The fatty acids are analyzed from lipids extracted from samples of a transgenic organism; the samples are homogenized in methanouchloroform (2:1, v/v) and the lipids extracted as described by Bligh and Dyer (1959) (Can J Biochem Physiol 31:911).

In another aspect, the enzyme activity is determined in tissue samples obtained from a transgenic organism as described above (see for example Engeseth, N et al. (1996) Planta 198: 238–245). For example, in plants, tissue samples include but are not limited to leaf samples (such as discs), stem and root samples, and developing and mature seed embryonic or endosperm tissue. Typically, tissue samples are incubated with either precursors of fatty acid synthesis, such as $^{14}$C-acetate, or with fatty acids, such as ammonium salts of $^{14}$C-fatty acids, which can be taken up and incorporated into tissue lipids. Additional co-factors for lipid synthesis, as required, are present during the incubation; such co-factors include but are not limited to ATP, CoA, $MgCl_2$, and lyso-phospholipids, such as lysoPC. Incubations generally proceed at room temperature in a buffered solution, such as 0.1M potassium phosphate at pH 7.2, for a suitable period of time. The samples are then washed in buffer, and the tissue samples homogenized in methanol/chloroform (2:1, v/v) and the lipids extracted as described by Bligh and Dyer (1959) (Can J Biochem Physiol 31:911).

In another aspect, the enzyme activity is determined in a sub-cellular fraction obtained from a transgenic organism as described above. For example, in plants, subcellular fractions may be obtained from any of the types of tissues described above, and include whole cell and microsomal membranes, plastids, and plastidial membrane fractions. Preparation of such fractions are well-known in the art. The subcellular fraction is then incubated with fatty acids, such as ammonium salts of 14C-fatty acids, which can be taken up and incorporated into tissue lipids. Additional co-factors for lipid synthesis, as required, are present during the incubation; such co-factors include but are not limited to ATP, CoA, $MgCl_2$, and lyso-phospholipids, such as lysoPC. The samples are incubated and the lipids extracted as described above.

In another aspect, the enzyme activity is determined from an in-vitro nucleic acid expression system, in which a nucleic acid sequence comprising SEQ ID NO: 1 or encoding a polypeptide comprising the amino acid sequence shown in SEQ ID NO: 2 is added and the encoded enzyme expressed. Such expression systems are well-known in the art, for example reticulocyte lysate or wheat germ. Because the enzyme is an integral membrane protein, it is necessary to include micellar or membrane structures into which the enzyme may be incorporated during or after protein synthesis. Moreover, because the enzyme in situ acts on a fatty acid esterified to a lipid, and requires cytochrome $b_5$ reductase and cytochrome b5 for activity, it is preferable that such micellar structures are obtained from sources which contain related lipid synthetic capabilities, such as from microsomes from plant tissues where the plant does not contain an endogenous fatty acid hydroxylase. Direct and quantitative measurements require the incorporation of labeled lipids into the micellar or membrane structures and the assurance that cytochrome $b_5$ and $b_5$ reductase are not limiting. The newly-expressed enzyme is then analyzed as described above for subcellular fractions.

The extracted lipid products of the oleate hydroxylase are analyzed by methods well-known in the art (Engeseth et al. (1996) Planta 198: 238–245; Broun et al (1997) Plant Physiol. 113: 933–942). For example, fatty acid methyl esters are prepared from an aliquot of the extracted lipid fraction by evaporating the solvent from the aliquot under N2, and resuspending and heating the lipids in 4% methanolic HCL (w/w). The fatty acid methyl esters are then separated, and for radioactive samples the radioactivity in each separated fraction determined, by radio gas-liquid chromatography (GLC) and radio-HPLC (Engeseth et al. (1996) Planta 198: 238–245). Alternatively, fatty acid methyl esters are prepared, derivatized with bis (trimethylsily)trifluoroacetamide:trimethyl-chlorosilane to obtain TMS fatty acid methyl esters of hydroxylated fatty acids and analyzed by GC (Broun et al (1997) Plant Physiol. 113: 933–942).

b. Purification of Oleate Hydroxylase

In some embodiments of the present invention, oleate hydroxylase polypeptides purified from recombinant organisms as described below are provided. In other embodiments, oleate hydroxylase polypeptides purified from in vitro transcription/translation expression systems as described above are provided. The present invention provides purified oleate hydroxylase polypeptides as well as fusion proteins thereof, as described below.

c. Chemical Synthesis of Oleate Hydroxylase

In other embodiments of the present invention, the protein itself is produced using chemical methods to synthesize either an entire oleate hydroxylase amino acid sequence or a portion thereof. For example, peptides are synthesized by solid phase techniques, cleaved from the resin, and purified by preparative high performance liquid chromatography (See for example, Creighton (1983) *Proteins Structures And Molecular Principles*, W H Freeman and Co, New York N.Y.). In other embodiments of the present invention, the composition of the synthetic peptides is confirmed by amino acid analysis or sequencing (See for example, Creighton, supra).

Direct peptide synthesis can be performed using various solid-phase techniques (Roberge et al. (1995) Science, 269:202–204) and automated synthesis may be achieved, for example, using ABI 431A Peptide Synthesizer (Perkin Elmer) in accordance with the instructions provided by the manufacturer. Additionally, the amino acid sequence of oleate hydroxylase, or any part thereof, may be altered during direct synthesis and/or combined using chemical methods with other sequences to produce a variant polypeptide.

d. Generation of Oleate Hydroxylase Antibodies

In some embodiments of the present invention, antibodies are generated to allow for the detection and characterization of oleate hydroxylase protein. The antibodies may be prepared using various immunogens. In one embodiment, the immunogen is an oleate hydroxylase peptide as depicted in SEQ ID NO: 2 to generate antibodies that recognize oleate hydroxylase. Such antibodies include, but are not limited to polyclonal, monoclonal, chimeric, single chain, Fab fragments, and Fab expression libraries.

Various procedures known in the art may be used for the production of polyclonal antibodies directed against oleate hydroxylase of the present invention. For the production of antibody, various host animals can be immunized by injection with the peptide corresponding to the oleate hydroxylase epitope including but not limited to rabbits, mice, rats, sheep, goats, etc. In a preferred embodiment, the peptide is conjugated to an immunogenic carrier (for example, diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (for example, aluminum hydroxide), surface active substances (for example, lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies directed toward oleate hydroxylase of the present invention, it is contemplated that any technique that provides for the production of antibody molecules by continuous cell lines in culture finds use with the present invention (See for example, Harlow and Lane, *Antibodies: A Laboratory Manual*, Cold Spring Harbor Laboratory Press, Cold Spring Harbor, NY). These include but are not limited to the hybridoma technique originally developed by Köhler and Milstein (Köhler and Milstein (1975) Nature, 256:495–497), as well as the trioma technique, the human B-cell hybridoma technique (See for example, Kozbor et al. (1983) Immunol. Tod., 4:72), and the EBV-hybridoma technique to produce human monoclonal antibodies (Cole et al., (1985) in *Monoclonal Antibodies and Cancer Therapy*, Alan R. Liss, Inc. pp. 77–96).

In the production of antibodies, it is contemplated that screening for the desired antibody is accomplished by techniques known in the art (for example, radioimmunoassay, ELISA (enzyme-linked immunosorbant assay), "sandwich" immunoassays, immunoradiometric assays, gel diffusion precipitin reactions, immunodiffusion assays, in situ immunoassays (for example, using colloidal gold, enzyme or radioisotope labels, for example), Western blots, precipitation reactions, agglutination assays (for example, gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.

In some embodiments of the present invention, the foregoing antibodies are used in methods known in the art relating to the expression of oleate hydroxylase (for example, for Western blotting), measuring levels thereof in appropriate biological samples, etc. The antibodies can be used to detect oleate hydroxylase in a biological sample from a plant. The biological sample can be an extract of a tissue, or a sample fixed for microscopic examination.

The biological samples are then be tested directly for the presence of oleate hydroxylase using an appropriate strategy (for example, ELISA or radioimmunoassay) and format (for example, microwells, dipstick as for example described in International Patent Publication WO 93/03367), etc. Alternatively, proteins in the sample can be size separated (for example, by polyacrylamide gel electrophoresis (PAGE), in the presence or not of sodium dodecyl sulfate (SDS), and the presence of the oleate hydroxylase detected by immunoblotting (Western blotting). Immunoblotting techniques are generally more effective with antibodies generated against a peptide corresponding to an epitope of a protein, and hence, are particularly suited to the present invention.

3. Expression of Cloned Oleate Hydroxylase

In other embodiment of the present invention, a nucleic acid sequence corresponding to SEQ ID NO: 1 or encoding a polypeptide comprising the amino acid sequence shown in SEQ ID NO: 2 are used to generate recombinant DNA molecules that direct the expression of the encoded protein product in appropriate host cells. In yet other embodiments, a nucleic acid sequence corresponding to the antisense sequence of SEQ ID NO: 1 or the antisense sequence of the nucleic acid sequence encoding SEQ ID NO: 2 are used.

As will be understood by those of skill in the art, it may be advantageous to produce SEQ ID NO:2-encoding nucleotide sequences possessing non-naturally occurring codons. Therefore, in some preferred embodiments, codons preferred by a particular prokaryotic or eukaryotic host (Murray et al. (1989) Nucl. Acids Res., 17) can be selected, for example, to increase the rate of SEQ ID NO:2 expression or to produce recombinant RNA transcripts having desirable properties, such as a longer half-life, than transcripts produced from naturally occurring sequence.

a. Vectors for Production of Oleate Hydroxylase

The nucleic acid sequences of the present invention may be employed for producing polypeptides by recombinant techniques. Thus, for example, the nucleic acid sequence may be included in any one of a variety of expression vectors for expressing a polypeptide. In some embodiments of the present invention, vectors include, but are not limited to, chromosomal, nonchromosomal and synthetic DNA sequences (for example, derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In particular, some embodiments of the present invention provide recombinant constructs comprising one or more of the nucleic sequences as described above (for example, SEQ ID NO: 1). In some embodiments of the present invention, the constructs comprise a vector, such as a plasmid or viral vector, into which a nucleic acid sequence of the invention has been inserted, in a forward or reverse orientation. In preferred embodiments of the present invention, the appropriate nucleic acid sequence is inserted into the vector using any of a variety of procedures. In general, the nucleic acid sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); and 2) Eukaryotic—pWLNEO, pSV2CAT, pOG44, PXT1, pSG (Stratagene) pSVK3, pBPV, pMSG, and pSVL (Pharmacia). Any other plasmid or vector may be used as long as they are replicable and viable in the host. In some preferred embodiments of the present invention, plant expression vectors comprise an origin of replication, a suitable promoter and enhancer, and also any necessary ribosome binding sites, polyadenylation sites, splice donor and acceptor sites, transcriptional termination sequences, and 5' flanking nontranscribed sequences. In other embodiments, DNA sequences derived from the SV40 splice, and polyadenylation sites may be used to provide the required nontranscribed genetic elements.

In certain embodiments of the present invention, the nucleic acid sequence in the expression vector is operatively linked to at least one suitable regulatory sequence. Such sequences include, but are not limited to, an appropriate expression control sequence(s) (promoter) to direct mRNA synthesis. Promoters useful in the present invention include, but are not limited to, the LTR or SV40 promoter, the *E. coli* lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. In other embodiments of the present invention, recombinant expression vectors include origins of replication and selectable markers permitting transformation of the host cell (for example, dihydrofolate reductase or neomycin resistance for eukaryotic cell culture, or tetracycline or ampicillin resistance in *E. coli*).

In some embodiments of the present invention, transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

b. Host Cells for Production Oleate Hydroxylase

In a further embodiment, the present invention provides host cells containing the above-described constructs. In some embodiments of the present invention, the host cell is a higher eukaryotic cell (for example, a plant cell). In other embodiments of the present invention, the host cell is a lower eukaryotic cell (for example, a yeast cell). In still other embodiments of the present invention, the host cell can be a prokaryotic cell (for example, a bacterial cell). Specific examples of host cells include, but are not limited to, *Escherichia coli, Salmonella typhimurium, Bacillus subtilis*, and various species within the genera *Pseudomonas, Streptomyces*, and *Staphylococcus*, as well as *Saccharomycees cerivisiae, Schizosaccharomycees pombe, Drosophila* S2 cells, Spodoptera Sf9 cells, Chinese hamster ovary (CHO) cells, COS-7 lines of monkey kidney fibroblasts, (Gluzman (1981) Cell 23:175), 293T, C127, 3T3, HeLa and BHK cell lines, NT-1 (tobacco cell culture line), root cell and cultured roots in rhizosecretion (Gleba et al. (1999) Proc Natl Acad Sci USA 96: 5973–5977) and other plant cells, which can be cultivated in fermenters or which can be regenerated into an entire plants.

The constructs in host cells can be used in a conventional manner to produce the gene product encoded by the recombinant sequence. In some embodiments, introduction of the construct into the host cell can be accomplished by calcium phosphate transfection, DEAE-Dextran mediated transfection, or electroporation (See for example, Davis et al. (1986) *Basic Methods in Molecular Biology*).

Proteins can be expressed in eukaryotic cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al. (1989) *Molecular Cloning: A Laboratory Manual, Second Edition*, Cold Spring Harbor, N.Y..

In some embodiments of the present invention, following transformation of a suitable host cell and growth of the host cell to an appropriate cell density, the selected promoter is induced by appropriate means (for example, temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells and other cultured cells employed in expression of proteins can be disrupted by any convenient method, including freeze-thaw cycling, sonication, mechanical disruption, or use of cell lysing agents.

c. Purification of Oleate Hydroxylase

The present invention also provides methods for recovering and purifying oleate hydroxylase from recombinant cell cultures or transgenic organisms. Purification typically begins by disruption of the cells, and preparation of cell fractions with the highest specific activity of the oleate hydroxylase. Because the oleate hydroxylase is a membrane-bound enzyme, it is contemplated that microsomal preparations contain the highest specific activity of the enzyme. Further purification of the oleate hydroxylase is then accomplished by detergent solubilization of the enzyme, followed by column chromatography. Purification schemes have been developed for related enzymes, such as plastidial oleate desaturase (Schmidt et al. (1994) Plant Molecular Biology 26: 631–642). Because the oleate hydroxylase exhibits a high degree of similarity to oleate desaturase, both in amino acid sequence and in the reaction catalyzed, the oleate hydroxylase is purified by a similar scheme to that reported for the desaturase. Alternative chromatographic steps include but are not limited to ammonium sulfate or ethanol precipitation, acid extraction, anion or cation exchange chromatography, phosphocellulose chromatography, hydrophobic interaction chromatography, affinity chromatography, hydroxylapatite chromatography, lectin chromatography, and size exclusion chromatography.

The present invention further provides nucleic acid sequences encoding SEQ ID NO: 2 (for example, SEQ ID NO: 1) fused in frame to a marker sequence that allows for expression alone or both expression and purification of the polypeptide of the present invention. A non-limiting example of a marker sequence is a hexahistidine tag that may be supplied by a vector, for example, a pQE-30 vector which adds a hexahistidine tag to the N terminal of the oleate hydroxylase of the present invention and which results in expression of the polypeptide in the case of a bacterial host, and more preferably by vector PT-23B, which adds a hexahistidine tag to the C terminal of the oleate hydroxylase of the present invention and which results in improved ease of purification of the polypeptide fused to the marker in the case of a bacterial host, In another non-limiting example, is the fusion of glutathione S-transferase to the enzyme, resulting in the expression of (GST)-oleate hydroxylase, such as was used by Maeng, CY et al. (2001) Biochem Biophys Res Commun: 282(3):787–92. Yet other non-limiting examples include a hemagglutinin (HA) tag as a marker sequence when a mammalian host is used. The HA tag corresponds to an epitope derived from the influenza hemagglutinin protein (Wilson et al. (1984) Cell, 37:767).

3. Fusion Proteins and Genes

The present invention also provides nucleic acid sequences encoding fusion proteins incorporating all or part of oleate hydroxylase, and the polypeptides encoded by such nucleic acid sequences. In some embodiments, the fusion proteins have an oleate hydroxylase functional domain with a fusion partner. Accordingly, in some embodiments of the present invention, the coding sequences for the polypeptide (for example, an oleate hydroxylase functional domain) is incorporated as a part of a fusion gene including a nucleotide sequence encoding a different polypeptide.

In some embodiments of the present invention, chimeric constructs code for a fusion protein comprising all or part of the oleate hydroxylase of the present invention, and all or a part of a cytochrome b5, such that each protein is active. Similar fusion proteins have been reported, as for example a cDNA isolated from ripening sunflower embryos which encoded a fusion protein, of which one portion was highly homologous to a membrane bound desaturase and the other N terminal portion was highly homologous to cytochrome b5 (Sperling et al. (1995) Eur. J. Biochem. 232: 798–805). Such a fusion, between the electron donor and its acceptor was speculated to increase efficiency of the electron transport required for desaturation (Sperling et al. (1995) Eur. J. Biochem. 232: 798–805). In a similar fashion, a fusion between an oleate hydroxylase of the present invention and a cytochrome b5 protein is contemplated to increase the efficiency of the electron transport required for the hydroxylation reaction, as well as to decrease the reliance of the enzyme upon added or exogenous or endogenous cytochrome b5 for its activity.

In other embodiments of the present invention, chimeric constructs code for fusion proteins containing an oleate hydroxylase of the present invention and at least a portion of another gene. In some embodiments, the fusion proteins have biological activity similar to the oleate hydroxylase of the present invention (for example, they have at least one desired biological activity of oleate hydroxylase). In other embodiments, the fusion proteins have altered biological activity In yet other embodiments, chimeric constructs code for fusion proteins containing an oleate hydroxylase of the present invention and a leader sequence. Such leader sequences are well-known in the art, and function to direct the protein to targeted cellular locations. Exemplary leader sequences include but are not limited to those disclosed in Gavel Y, and von Heijne G (1990) FEBS Lett 261(2):455, and Emanuelsson O et al. (2000) J Mol Biol 300:1005–16.

In addition to utilizing fusion proteins to alter biological activity, it is widely appreciated that fusion proteins can also facilitate the expression and/or purification of proteins, such as the oleate hydroxylase protein of the present invention. Accordingly, in some embodiments of the present invention, oleate hydroxylase is generated as a glutathione-S-transferase (in other words, a GST fusion protein). It is contemplated that such GST fusion proteins facilitates purification of oleate hydroxylase, such as by the use of glutathione-derivatized matrices (See for example, Ausabel et al., eds.(1991) *Current Protocols in Molecular Biology*, John Wiley & Sons, NY).

In another embodiment of the present invention, a fusion gene coding for a purification leader sequence, such as a poly-(His)/enterokinase cleavage site sequence at the N-terminus of the desired portion of oleate hydroxylase allows purification of the expressed hydroxylase fusion protein by affinity chromatography using a $Ni^{2+}$ metal resin. In still another embodiment of the present invention, the purification leader sequence is then subsequently removed by treatment with enterokinase (See for example, Hochuli et al. (1987) J. Chromatogr., 411:177; and Janknecht et al., Proc. Natl. Acad. Sci. USA, 88:8972). In yet other embodiments of the present invention, a fusion gene coding for a purification sequence appended to either the N or the C terminus allows for affinity purification; one example is addition of a hexahistidine tag to the carboxy terminus of oleate hydroxylase which was optimal for affinity purification, as described in Example 3A.

Techniques for making fusion genes are well known. Essentially, the joining of various nucleic acid fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment of the present invention, the fusion gene can be synthesized by conventional techniques including automated DNA synthesizers. Alternatively, in other embodiments of the present invention, PCR amplification of gene fragments is carried out using anchor primers that give rise to complementary overhangs between two consecutive gene fragments that can subsequently be annealed to generate a chimeric gene sequence (See for example, Current Protocols in Molecular Biology, supra).

Fusion proteins may be cloned and expressed as described above.

B. Production of Large Quantities of Hydroxy-Oleate

In one aspect of the present invention, methods are provided for producing large quantities of hydroxy-oleate. In some embodiments, hydroxy-oleates are produced in vivo, in organisms transformed with a heterologous gene encoding an oleate hydroxylase of the present invention and capable of expressing hydroxylase activity, and grown under conditions sufficient to effect production of hydroxy-oleates. In other embodiments, hydroxy-oleates are produced in vitro, from either nucleic acid sequences encoding oleate hydroxylase of the present invention or from polypeptides comprising the amino acid sequence shown in SEQ ID NO: 2 and exhibiting oleate hydroxylase activity 1. In Vivo in Transgenic Organism In some embodiments of the present invention, hydroxy-oleates are produced in vivo, by providing an organism transformed with a heterologous gene encoding an oleate hydroxylase of the present invention and growing the transgenic organism under conditions sufficient to effect production of hydroxy-oleates. In other embodiments of the present invention, hydroxy-oleates are produced in vivo by transforming an organism with a heterologous gene encoding an oleate hydroxylase of the present invention and growing the transgenic organism under conditions sufficient to effect production of hydroxy-oleates.

Organisms which are transformed with a heterologous gene encoding an oleate hydroxylase of the present invention include preferably those which naturally synthesize and store in some manner fatty acids, and those which are commercially feasible to grow and suitable for harvesting the fatty acid products. Such organisms include but are not limited to bacteria and plants. Examples of bacteria include *E. coli* and related bacteria which can be grown in commercial-scale fermenters. Examples of plants include preferably oil-producing plants; examples of such plants include but are not limited to soybean, rapeseed and canola, sunflower, cotton, corn, cocoa, safflower, oil palm, coconut palm, flax, castor, and peanut. Non-commercial cultivars of plants can be transformed, and the trait for expression of an oleate hydroxylase of the present invention moved to commercial cultivars by breeding techniques well-known in the art.

A heterologous gene encoding an oleate-hydroxylase of the present invention, which includes fusion proteins, includes any suitable sequence as described previously. Preferably, the heterologous gene is provided within an expression vector such that transformation with the vector results in expression of the polypeptide; suitable vectors are described previously and subsequently.

A transgenic organism is grown under conditions sufficient to effect production of hydroxy-oleates. In some embodiments of the present invention, a transgenic organism is supplied with exogenous substrates of the hydroxy-oleates. Such substrates comprise mono-, di-, and tri-unsaturated fatty acids; the chain length of such unsaturated fatty acids is variable, but is preferably 18 carbons in length. The unsaturated fatty acids may also comprise additional functional groups, including but not limited to acetylenic bonds, conjugated acetylenic and ethylenic bonds, allenic, groups, cyclopropane, cyclopropene, cyclopentene and furan rings, epoxy-, and keto-groups and double bonds of both the cis and trans configuration and separated by more than one methylene group; two or more of these functional groups may be found in a single fatty acid. The substrates are added or present as the free acids, the ACP and CoA esters, the salts of these acids, the glycerolipid esters (particularly the phospholipid and triacylglycerol esters), the wax esters, and the ether derivatives of these acids. Most preferably, such substrates are selected from the group consisting of: $16:1^{d9}$ (palmitoleate); $18:1^{d6}$ (petroselenate); $18:1^{d9}$ (oleate); $20:1^{d11}$ (gladoleate or eicosenoate); and $22:1^{d13}$ (erucate or docosenoate). Substrates may be supplied in various forms as are well known in the art; such forms include aqueous suspensions prepared by sonication, aqueous suspensions prepared with detergents and other surfactants, micellar preparations which include the substrate, dissolution of the substrate into a solvent, and dried powders of substrates. Such forms may be added to organisms or cultured cells or tissues grown in fermenters, or may be applied to larger organisms, such as pot- or field-grown plants, by any of several known techniques, such as by irrigating, spraying, or fumigating.

In yet other embodiments of the present invention, a transgenic organism comprises a heterologous gene encoding an oleate hydroxylase of the present invention operably linked to an inducible promoter, and is grown either in the presence of the an inducing agent, or is grown and then exposed to an inducing agent. In still other embodiments of the present invention, a transgenic organism comprises a heterologous gene encoding an oleate hydroxylase of the present invention operably linked to a promoter which is either tissue specific or developmentally specific, and is grown to the point at which the tissue is developed or the developmental stage at which the developmentally-specific promoter is activated.

In alternative embodiments, a transgenic organism as described above is engineered to produce greater amounts of the fatty acid substrate. Organisms include bacteria, yeast, algae and plants; preferably, the organism is a plant; most preferably, the organism is an oil-producing plant.

In other embodiments of the present invention, the methods for producing large quantities of hydroxy-oleates further comprise collecting the hydroxy-oleates produced. Such methods are known generally in the art, and include harvesting the transgenic organisms and extracting the hydroxy-oleates. Extraction procedures preferably include solvent extraction, and typically include disrupting cells, as by chopping, mincing, grinding, and/or sonicating, prior to solvent extraction. Solvent extraction procedures have been described previously. In yet other embodiments of the present invention, the hydroxy-oleates are further purified, as for example by thin layer liquid chromatography, gas-liquid chromatography, or high pressure liquid chromatography a. Transgenic Plants, Seeds, and Plant Parts In one preferred aspect of the invention, hydroxy-oleates are produced in transgenic plants; preferably, the hydroxy-oleates are produced in plant seed oils. Plants are transformed with a heterologous gene encoding an oleate hydroxylase of the present invention or transformed with a fusion gene encoding a fusion polypeptide comprising an oleate hydroxylase of the present invention according to procedures well known in the art. It is contemplated that the heterologous genes are utilized to increase the level of the enzyme activities encoded by the heterologous genes.

a1. Plants

The methods of the present invention are not limited to any particular plant. Indeed, a variety of plants are contemplated, including but not limited to soybean (*Glycine max*), rapeseed and canola (including *Brassica napus* and *B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*) and peanut (*Arachis hypogaea*). The group also includes non-agronomic species which are useful in developing appropriate expression vectors such as tobacco, rapid cycling Brassica species, and *Arabidopsis thaliana*, and wild species which may be a source of unique fatty acids.

a2. Vectors

The methods of the present invention contemplate the use of a heterologous gene encoding an oleate hydroxylase of the present invention, as described previously.

Heterologous genes intended for expression in plants are first assembled in expression cassettes comprising a promoter. Methods which are well known to those skilled in the art may be used to construct expression vectors containing a heterologous gene and appropriate transcriptional and translational control elements. These methods include in vitro recombinant DNA techniques, synthetic techniques, and in vivo genetic recombination. Such techniques are widely described in the art (See for example, Sambrook. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y).

In general, these vectors comprise a nucleic acid sequence encoding an oleate hydroxylase of the present invention (as described above) operably linked to a promoter and other regulatory sequences (for example, enhancers, polyadenylation signals, etc.) required for expression in a plant.

Promoters include but are not limited to constitutive promoters, tissue-, organ-, and developmentally-specific promoters, and inducible promoters. Examples of promoters include but are not limited to: constitutive promoter 35S of cauliflower mosaic virus; a wound-inducible promoter from tomato, leucine amino peptidase ("LAP," Chao et al. (1999) Plant Physiol 120: 979–992); a chemically-inducible promoter from tobacco, Pathogenesis-Related 1 (PR1) (induced by salicylic acid and BTH (benzothiadiazole-7-carbothioic acid S-methyl ester)); a tomato proteinase inhibitor II promoter (PIN2) or LAP promoter (both inducible with methyl jasmonate); a heat shock promoter (U.S. Pat. No. 5,187, 267); a tetracycline-inducible promoter (U.S. Pat. No. 5,057, 422); and seed-specific promoters, such as those for seed storage proteins (for example, phaseolin, napin, oleosin, and a promoter for soybean beta conglycin (Beachy et al. (1985) EMBO J. 4: 3047–3053)). All references cited herein are incorporated in their entirety.

The expression cassettes may further comprise any sequences required for expression of mRNA. Such sequences include, but are not limited to transcription terminators, enhancers such as introns, viral sequences, and sequences intended for the targeting of the gene product to specific organelles and cell compartments.

A variety of transcriptional terminators are available for use in expression of sequences using the promoters of the present invention. Transcriptional terminators are responsible for the termination of transcription beyond the transcript and its correct polyadenylation. Appropriate transcriptional terminators and those which are known to function in plants include, but are not limited to, the CaMV 35S terminator, the tml terminator, the pea rbcS E9 terminator, and the nopaline and octopine synthase terminator (See for example, Odell et al. (1985) Nature 313:810; Rosenberg et al. (1987) Gene, 56:125; Guerineau et al. (1991) Mol. Gen. Genet., 262:141 Proudfoot (1991) Cell, 64:671; Sanfacon et al., Genes Dev., 5:141; Mogen et al. (1990) Plant Cell, 2:1261; Munroe et al. (1990) Gene, 91:151; Ballas et al. (1989) Nucleic Acids Res. 17:7891; Joshi et al. (1987) Nucleic Acid Res., 15:9627).

In addition, in some embodiments, constructs for expression of the heterologous gene of interest include one or more of sequences found to enhance gene expression from within the transcriptional unit. These sequences can be used in conjunction with the nucleic acid sequence of interest to increase expression in plants. Various intron sequences have been shown to enhance expression, particularly in monocotyledonous cells. For example, the introns of the maize Adh1 gene have been found to significantly enhance the expression of the wild-type gene under its cognate promoter when introduced into maize cells (Callis et al. (1987) Genes Develop. 1:1183). Intron sequences have been routinely incorporated into plant transformation vectors, typically within the non-translated leader.

In some embodiments of the present invention, the construct for expression of the nucleic acid sequence of interest also includes a regulator such as a nuclear localization signal (Kalderon et al. (1984) Cell 39:499; Lassner et al. (1991) Plant Molecular Biology 17:229), a plant translational consensus sequence (Joshi (1987) Nucleic Acids Research 15:6643), an intron (Luehrsen and Walbot (1991) Mol. Gen. Genet. 225:81), and the like, operably linked to the nucleic acid sequence encoding the oleate hydroxylase of the present invention.

In preparing the construct comprising the nucleic acid sequence encoding an oleate hydroxylase of the present invention, various DNA fragments can be manipulated, so as to provide for the DNA sequences in the desired orientation (for example, sense or antisense) orientation and, as appropriate, in the desired reading frame. For example, adapters or linkers can be employed to join the DNA fragments or other manipulations can be used to provide for convenient restriction sites, removal of superfluous DNA, removal of restriction sites, or the like. For this purpose, in vitro mutagenesis, primer repair, restriction, annealing, resection, ligation, or the like is preferably employed, where insertions, deletions or substitutions (for example, transitions and transversions) are involved.

Numerous transformation vectors are available for plant transformation. The selection of a vector for use will depend upon the preferred transformation technique and the target species for transformation. For certain target species, different antibiotic or herbicide selection markers are preferred. Selection markers used routinely in transformation include the nptII gene which confers resistance to kanamycin and related antibiotics (Messing and Vierra (1982) Gene 19: 259; Bevan et al. (1983) Nature 304:184), the bar gene which confers resistance to the herbicide phosphinothricin (White et al. (1990) Nucl Acids Res. 18:1062; Spencer et al. (1990) Theor. Appl. Genet. 79: 625), the hph gene which confers resistance to the antibiotic hygromycin (Blochlinger and Diggelmann (1984) Mol. Cell. Biol. 4:2929), and the dhfr gene, which confers resistance to methotrexate (Bourouis et al. (1983) EMBO J., 2:1099).

In some preferred embodiments, the vector is adapted for use in an Agrobacterium mediated transfection process (See for example, U.S. Pat. Nos. 5,981,839; 6,051,757; 5,981, 840; 5,824,877; and 4,940,838; all of which are incorporated herein by reference). Construction of recombinant Ti and Ri plasmids in general follows methods typically used with the more common bacterial vectors, such as pBR322. Additional use can be made of accessory genetic elements sometimes found with the native plasmids and sometimes constructed from foreign sequences. These may include but are not limited to structural genes for antibiotic resistance as selection genes.

There are two systems of recombinant Ti and Ri plasmid vector systems now in use. The first system is called the "cointegrate" system. In this system, the shuttle vector containing the gene of interest is inserted by genetic recombination into a non-oncogenic Ti plasmid that contains both the cis-acting and trans-acting elements required for plant transformation as, for example, in the pMLJ1 shuttle vector and the non-oncogenic Ti plasmid pGV3850. The second system is called the "binary" system in which two plasmids are used; the gene of interest is inserted into a shuttle vector containing the cis-acting elements required for plant transformation. The other necessary functions are provided in trans by the non-oncogenic Ti plasmid as exemplified by the pBIN19 shuttle vector and the non-oncogenic Ti plasmid PAL4404. Some of these vectors are commercially available.

In other embodiments of the invention, the nucleic acid sequence of interest is targeted to a particular locus on the plant genome. Site-directed integration of the nucleic acid sequence of interest into the plant cell genome may be achieved by, for example, homologous recombination using Agrobacterium-derived sequences. Generally, plant cells are incubated with a strain of Agrobacterium which contains a targeting vector in which sequences that are homologous to a DNA sequence inside the target locus are flanked by Agrobacterium transfer-DNA (T-DNA) sequences, as previously described (U.S. Pat. No. 5,501,967). One of skill in the art knows that homologous recombination may be achieved using targeting vectors which contain sequences that are homologous to any part of the targeted plant gene, whether belonging to the regulatory elements of the gene, or the coding regions of the gene. Homologous recombination may be achieved at any region of a plant gene so long as the nucleic acid sequence of regions flanking the site to be targeted is known.

In yet other embodiments, the nucleic acids of the present invention is utilized to construct vectors derived from plant (+) RNA viruses (for example, brome mosaic virus, tobacco mosaic virus, alfalfa mosaic virus, cucumber mosaic virus, tomato mosaic virus, and combinations and hybrids thereof). Generally, the inserted oleate hydroxylase polynucleotide can be expressed from these vectors as a fusion protein (for example, coat protein fusion protein) or from its own subgenomic promoter or other promoter. Methods for the construction and use of such viruses are described in U.S. Pat. Nos. 5,846,795; 5,500,360; 5,173,410; 5,965,794; 5,977,438; and 5,866,785, all of which are incorporated herein by reference.

In some embodiments of the present invention, where the nucleic acid sequence of interest is introduced directly into a plant. One vector useful for direct gene transfer techniques in combination with selection by the herbicide Basta (or phosphinothricin) is a modified version of the plasmid pCIB246, with a CaMV 35S promoter in operational fusion to the E. coli GUS gene and the CaMV 35S transcriptional terminator (WO 93/07278).

a3. Transformation Techniques

Once a nucleic acid sequence encoding an oleate hydroxylase of the present invention is operatively linked to an appropriate promoter and inserted into a suitable vector for the particular transformation technique utilized (for example, one of the vectors described above), the recombinant DNA described above can be introduced into the plant cell in a number of art-recognized ways. Those skilled in the art will appreciate that the choice of method might depend on the type of plant targeted for transformation. In some embodiments, the vector is maintained episomally. In other embodiments, the vector is integrated into the genome.

In some embodiments, direct transformation in the plastid genome is used to introduce the vector into the plant cell (See for example, U.S. Pat. Nos. 5,451,513; 5,545,817; 5,545,818; PCT application WO 95/16783). The basic technique for chloroplast transformation involves introducing regions of cloned plastid DNA flanking a selectable marker together with the nucleic acid encoding the RNA sequences of interest into a suitable target tissue (for example, using biolistics or protoplast transformation with calcium chloride or PEG). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps 12 genes conferring resistance to spectinomycin and/or streptomycin are utilized as selectable markers for transformation (Svab et al. (1990) PNAS, 87:8526; Staub and Maliga (1992) Plant Cell, 4:39). The presence of cloning sites between these markers allowed creation of a plastid targeting vector introduction of foreign DNA molecules (Staub and Maliga, (1993) EMBO J., 12:601). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab and Maliga (1993) PNAS, 90:913). Other selectable markers useful for plastid transformation are known in the art and encompassed within the scope of the present invention. Plants homoplasmic for plastid genomes containing the two nucleic acid sequences separated by a promoter of the present invention are obtained, and are preferentially capable of high expression of the RNAs encoded by the DNA molecule.

In other embodiments, vectors useful in the practice of the present invention are microinjected directly into plant cells by use of micropipettes to mechanically transfer the recombinant DNA (Crossway (1985) Mol. Gen. Genet, 202:179). In still other embodiments, the vector is transferred into the plant cell by using polyethylene glycol (Krens et al. (1982) Nature, 296:72; Crossway et al. (1986) BioTechniques, 4:320); fusion of protoplasts with other entities, either minicells, cells, lysosomes or other fusible lipid-surfaced bodies (Fraley et al. (1982) Proc. Natl. Acad. Sci., USA, 79:1859); protoplast transformation (EP 0 292 435); direct gene transfer (Paszkowski et al. (1984) EMBO J., 3:2717; Hayashimoto et al. (1990) Plant Physiol. 93:857).

In still further embodiments, the vector may also be introduced into the plant cells by electroporation. (Fromm, et al. (1985) Pro. Natl Acad. Sci. USA 82:5824; Riggs et al. (1986) Proc. Natl. Acad. Sci. USA 83:5602). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

In yet other embodiments, the vector is introduced through ballistic particle acceleration using devices (for example, available from Agracetus, Inc., Madison, Wis. and Dupont, Inc., Wilmington, Del.). (See for example, U.S. Pat. No. 4,945,050; and McCabe et al. (1988) Biotechnology 6:923). See also, Weissinger et al. (1988) Annual Rev. Genet. 22:421; Sanford et al. (1987) Particulate Science and Technology, 5:27 (onion); Svab et al. (1990) Proc. Natl. Acad. Sci. USA, 87:8526 (tobacco chloroplast); Christou et al. (1988) Plant Physiol., 87:671 (soybean); McCabe et al. (1988) Bio/Technology 6:923 (soybean); Klein et al. (1988) Proc. Natl. Acad. Sci. USA, 85:4305 (maize); Klein et al. (1988) Bio/Technology, 6:559 (maize); Klein et al. (1988) Plant Physiol., 91:4404 (maize); Fromm et al. (1990) Bio/Technology, 8:833; and Gordon-Kamm et al. (1990) Plant Cell, 2:603 (maize); Koziel et al. (1993) Biotechnology, 11:194 (maize); Hill et al. (1995) Euphytica, 85:119 and Koziel et al. (1996) Annals of the New York Academy of Sciences 792:164; Shimamoto et al. (1989) Nature 338: 274 (rice); Christou et al. (1991) Biotechnology, 9:957 (rice);

Datta et al. (1990) Bio/Technology 8:736 (rice); European Patent Application EP 0 332 581 (orchardgrass and other Pooideae); Vasil et al. (1993) Biotechnology, 11: 1553 (wheat); Weeks et al. (1993) Plant Physiol., 102: 1077 (wheat); Wan et al. (1994) Plant Physiol. 104: 37 (barley); Jahne et al. (1994) Theor. Appl. Genet. 89:525 (barley); Knudsen and Muller (1991) Planta, 185:330 (barley); Umbeck et al. (1987) Bio/Technology 5: 263 (cotton); Casas et al. (1993) Proc. Natl. Acad. Sci. USA 90:11212 (sorghum); Somers et al. (1992) Bio/Technology 10:1589 (oat); Torbert et al. (1995) Plant Cell Reports, 14:635 (oat); Weeks et al. (1993) Plant Physiol., 102:1077 (wheat); Chang et al., WO 94/13822 (wheat) and Nehra et al. (1994) The Plant Journal, 5:285 (wheat).

In addition to direct transformation, in some embodiments, the vectors comprising a nucleic acid sequence encoding an oleate hydroxylase of the present invention are transferred using *Agrobacterium*-mediated transformation (Hinchee et al. (1988) Biotechnology, 6:915; Ishida et al. (1996) Nature Biotechnology 14:745). *Agrobacterium* is a representative genus of the gram-negative family Rhizobiaceae. Its species are responsible for plant tumors such as crown gall and hairy root disease. In the dedifferentiated tissue characteristic of the tumors, amino acid derivatives known as opines are produced and catabolized. The bacterial genes responsible for expression of opines are a convenient source of control elements for chimeric expression cassettes. Heterologous genetic sequences (for example, nucleic acid sequences operatively linked to a promoter of the present invention), can be introduced into appropriate plant cells, by means of the Ti plasmid of *Agrobacterium tumefaciens*. The Ti plasmid is transmitted to plant cells on infection by *Agrobacterium tumefaciens*, and is stably integrated into the plant genome (Schell (1987) Science, 237: 1176). Species which are susceptible infection by *Agrobacterium* may be transformed in vitro.

a4. Regeneration

After selecting for transformed plant material which can express the heterologous gene encoding an oleate hydroxylase of the present invention, whole plants are regenerated. Plant regeneration from cultured protoplasts is described in Evans et al. (1983) *Handbook of Plant Cell Cultures*, Vol. 1; (MacMillan Publishing Co. New York); and Vasil I. R. (ed.) (1984) *Cell Culture and Somatic Cell Genetics of Plants*, Acad. Press, Orlando, Vol. I, 1984, and Vol. III. It is known that many plants can be regenerated from cultured cells or tissues, including but not limited to all major species of sugarcane, sugar beet, cotton, fruit and other trees, legumes and vegetables, and monocots (for example, the plants described above). Means for regeneration vary from species to species of plants, but generally a suspension of transformed protoplasts containing copies of the heterologous gene is first provided. Callus tissue is formed and shoots may be induced from callus and subsequently rooted.

Alternatively, embryo formation can be induced from the protoplast suspension. These embryos germinate and form mature plants. The culture media will generally contain various amino acids and hormones, such as auxin and cytokinins. Shoots and roots normally develop simultaneously. Efficient regeneration will depend on the medium, on the genotype, and on the history of the culture. The reproducibility of regeneration depends on the control of these variables.

a5. Generation of Transgenic Lines

Transgenic lines are established from transgenic plants by tissue culture propagation. The presence of nucleic acid sequences encoding an oleate hydroxylase of the present invention or a fusion protein comprising the oleate hydroxylase may be transferred to related varieties by traditional plant breeding techniques.

b. Micro-Organisms

In another preferred aspect of the invention, hydroxyoleates are produced in transgenic mircoorganisms. Microorganisms are transformed with a heterologous gene encoding an oleate hydroxylase of the present invention or a gene encoding a fusion polypeptide comprising an oleate hydroxylase of the present invention according to procedures well known in the art. It is contemplated that the heterologous genes are utilized to increase the level of the enzyme activities encoded by the heterologous genes.

1. Yeast

In one embodiment, hydroxy fatty acids are produced in transgenic yeast. Wild-type yeast do not accumulate detectable concentrations of hydroxylated fatty acids. A nucleic acid sequence encoding an oleate-hydroxylase of the present invention is placed into an expression vector under transcriptional control of a promoter; for example, such a promoter is an inducible promoter GAL1. Expression of the enzyme is induced, and hydroxy fatty acids produced as a result of the enzyme activity.

2. In Vitro Systems

In other embodiments of the present invention, hydroxyoleates are produced in vitro, from either nucleic acid sequences encoding an oleate hydroxylase of the present invention or from a polypeptide comprising SEQ ID NO: 2 and exhibiting oleate hydroxylase activity.

a. Using Nucleic Acid Sequences Encoding SEQ ID NO: 2

In some embodiments of the present invention, methods for producing large quantities of hydroxy-oleates comprise adding an isolated nucleic acid sequence encoding an oleate hydroxylase of the present invention to in vitro expression systems under conditions sufficient to cause production of oleate hydroxylase. The isolated nucleic acid sequences encoding an oleate hydroxylase of the present invention is any suitable sequence as described previously, and preferably is provided within an expression vector such that addition of the vector to an in vitro transcription/translation system results in expression of the polypeptide. The system further comprises the substrates for oleate hydroxylase, as previously described. Alternatively, the system further comprises the means for generating the substrates for oleate.

In other embodiments of the present invention, the methods for producing large quantities of hydroxy-oleates further comprise collecting the hydroxy-oleates produced. Such methods are known generally in the art, and have been described previously. In yet other embodiments of the present invention, the hydroxy-oleates are further purified, as for example by thin layer liquid chromatography, gas-liquid chromatography, or high performance liquid chromatography.

b. Using Oleate Hydroxylase of the Present Invention

In some embodiments of the present invention, methods for producing large quantities of hydroxy-oleates comprise incubating an oleate hydroxylase of the present invention under conditions sufficient to result in the synthesis of hydroxy-oleates; generally, such incubation is carried out in a mixture which comprises the oleate hydroxylase.

An oleate hydroxylase, as described previously, is obtained by purification of either naturally occurring oleate hydroxylase of the present invention or recombinant oleate hydroxylase from an organism transformed with heterologous gene encoding an oleate hydroxylase of the present invention, as previously described. A source of naturally occurring oleate hydroxylase of the present invention includes but is not limited to castor bean endosperm. A source of recombinant oleate hydroxylase is either plant, bacterial or other transgenic organisms, transformed with a heterologous gene encoding an oleate hydroxylase of the present invention as described previously. The recombinant oleate hydroxylase may include means for improving purification, as for example a 6x-His tag added to the C-terminus of the protein as described previously. Alternatively, an oleate hydroxylase of the present invention is chemically synthesized.

The incubation mixture further comprises the substrates for oleate hydroxylase, as described previously. Alternatively, the mixture further comprises the means for generating the substrates for oleate hydroxylase.

In other embodiments of the present invention, the methods for producing large quantities of hydroxy-oleates further comprise collecting the hydroxy-oleates produced; such methods are described previously.

C. Disruption of Oleate Hydroxylase Activity

It is also contemplated that the nucleic acid sequences of the present invention may be utilized to decrease the level of oleate hydroxylase mRNA and/or protein in transfected cells as compared to the levels in wild-type cells.

Accordingly, in some embodiments of the present invention, the oleate hydroxylase nucleic acid sequences are utilized to decrease the level of oleate hydroxylase protein or mRNA in transgenic plants, plant tissues, or plant cells as compared to wild-type plants, plant tissues, or plant cells. One method of reducing oleate hydroxylase expression utilizes expression of antisense transcripts. Antisense RNA has been used to inhibit plant target genes in a tissue-specific manner (for example, van der Krol et al. (1988) Biotechniques 6:958–976). Antisense inhibition has been shown using the entire cDNA sequence as well as a partial cDNA sequence (for example, Sheehy et al. (1988) Proc. Natl. Acad. Sci. USA 85:8805–8809; Cannon et al. (1990) Plant Mol. Biol. 15:39–47). There is also evidence that 3' non-coding sequence fragment and 5' coding sequence fragments, containing as few as 41 base-pairs of a 1.87 kb cDNA, can play important roles in antisense inhibition (Ch'ng et al. (1989) Proc. Natl. Acad. Sci. USA 86:10006–10010).

Another method of reducing oleate hydroxylase expression utilizes the phenomenon of cosuppression or gene silencing (See for example, U.S. Pat. No. 6,063,947, incorporated herein by reference). The phenomenon of cosuppression has also been used to inhibit plant target genes in a tissue-specific manner. Cosuppression of an endogenous gene using a full-length cDNA sequence as well as a partial cDNA sequence (730 bp of a 1770 bp cDNA) are known (for example, Napoli et al. (1990) Plant Cell 2:279–289; van der Krol et al. (1990) Plant Cell 2:291–299; Smith et al. (1990) Mol. Gen. Genetics 224:477–481).

EXAMPLES

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); µM (micromolar); mol (moles); mmol (millimoles); µmol (micromoles); nmol (nanomoles); pmol (picomoles); g (grams); mg (milligrams); µg (micrograms); ng (nanograms); l or L (liters); ml (milliliters); µl (microliters); cm (centimeters); mm (millimeters); µm (micrometers); nm (nanometers); ° C. (degrees Centigrade); PCR (polymerase chain reaction); RT-PCR (reverse-transcriptase-PCR); TAIL-PCR (thermal asymmetric interlaced-PCR).

Example 1

Oleate Hydroxylase Gene Isolation and Use in Plant Transformation

The oleate hydroxylase isoform of the present invention was isolated from natural source castor cDNA corresponding to seed RNA. Its sequence was determined, and discovered to be novel with respect to sequences previously reported. The enzyme of the present invention carries a point mutation at codon 176 that encodes a leucine in place of the serine present in the previously described gene. Therefore, the novel oleate hydroxylase isoform is referred to as CasOH S176L.

Isolation of Castor Hydroxylase Isoform CasOH S176L

RNA was extracted from EJW 1993 and FVD 1990 castor endosperm (which are two separate batches of endosperm stored at −80° C.) using Biotechniques 1990 8:148 protocol modified for plants. Four First Strand cDNA Synthesis reactions were performed using BRL SuperScript. First Strand cDNA from the first two reactions were pooled and subjected to PCR using Advantage Polymerase (Clontech) protocol and Perkin Elmer Thermocycler (serial#P3629) with primer pairs 5 pf/3 pr and 5 pvaf/3 pvar, as shown and described further below. PCR fragments cloned into pCRII, Invitrogen TA vector reactions 1 and 2.

The folloing primers used in the PCR reaction are shown 5'–3'

The first two primers, 5pf and 3pf, were generated with the native sequence:

```
5pr  = GATCAAGCTTCCCGGGCCATGGGAGGTGGT    (SEQ ID NO:3)
             GGTCGCATGTCTACTGTCATAACCAGCAAC

3pr  = GATCGAGCTCGGATCCTTAATACTTGTTCC    (SEQ ID NO:4)
             GGTACCAGAAAACGCCTTGTGTAGGGGCTCCTTCATCTGGC
```

The next two primers, 5 pvaf and 3 pvar, were generated with the native sequence except for one valine to alanine substitution (underlined) in each.

```
5pvaf = GATCAAGCTTCCCGGGCCATGGGAGGTG     (SEQ ID NO:5)
              GTGGTCGCATGTCTACTGCCATAACCAGCAAC 3pvar = GATCGAGCTCGGATCCTTAATACTTGTT     (SEQ ID NO:6)
              CCGGTACCAGAAAGCGCCTTGTGTAGGGGCTCCTTCATCTGGC
```

Clones were analyzed by restriction with XhoI for to identity positive clones with correct orientation; two clones, 1.2 and 2.1, were identified and used further. ABI sequencing indicated that clone 1.2 contained S176L and E159K (a point mutation), and that clone 2.1 contained S176L and end primer mutations. Point mutations and end primer introduced mutations were eliminated by Cut and Paste cloning of clones 1.2 and 2.1, resulting in the creation of novel clones 1.1 to 1.6 containing S176L with BsteII @ 113 and HpaI @ 799. ABI sequencing of novel clones 1.1 and 1.2 indicated that the castor oleate hydroxylase encoded by these clones was S176L. The nucleic acid sequence encoding the novel oleate hydroxylase is shown in SEQ ID NO:1, and the amino acid sequence of the novel hydroxylase is shown in SEQ ID NO: 2.

Clone 1.2 was recloned back into pCRII for correct BamHI orientation, resulting in clone 1.2 CasOH pCRII positive, and the resulting BamHI fragment was cloned into a plant expression vector pPHAS. Clone 1.2.6 CasOH pPHAS was determined to be positive for expression orientation.

Cone 1.2.6 CasOH pHAS was restricted with PmeI and SbfI and cloned into pOEA1. The resulting CasOH pOEA1 clones 1.8, 1.11–1.15, and 1.17 were all confirmed by PCR and restriction analysis to be positive for vector and insert. ABI sequencing of clones CasOH pOEA1 1.8, 1.11, and 1.12 confirmed the presence of S176L mutation in each of these clones.

Transformation of Plants with Castor Hydroxylase Isoform CasOH S176L

Clones CasOH pOEA1 1.8, 1.11, and 1.12 were transformed into Agrobacteria GV3101 pMP90 by electroporation. Positive *Agrobacterium* transformants were identified by restriction and PCR analysis of DNA prepared from these bacteria, and Dositive transformants included 1.8.1–0.3, 1.11.1–3 CasOH pOEA1 *Agrobacterium*.

Several strains of Arabidopsis were transformed with 1.8.1 CasOH pOEA1 Agro. The Arabidopsis strains included wt (wild type), fad2 (oleate desaturase mutant) and fael (elongase mutant). Transformation was conducted by dipping and vacuum infiltration techniques (Bouchez et al. (1993) Acad. Sci. Ser. Iii 316: 1188). First generation transformed seeds (T1) were grown on soil in flats. Seedlings 2 weeks post emergence were sprayed with a 1:1000 dilution of the commercial herbicide formulation "Finale" containing gluphosinate ammonium. Arial portions of plants were resprayed a total of three times at approximately one week intervals. Surviving plants were screened by PCR using two primer pairs simultaneously. One pair was to identify the Pat (phosphinothricin acetyltransferase) portion of the plasmid, the other pair was specific for the inserted gene (the OEA castor hydroxylase). Three plants that satisfied these criteria were grown in the greenhouse and seeds were collected from individual plants.

Fatty acids were extracted from seeds by incubation with methanolic HCl and the hydroxy moiety derivatized with the use of BSTFA-TMCS (bis(trimethylsilyl) trifluoroacetamide)-(trimethylchlorosilane). These samples were analyzed by GC/MS, and the peaks were identified by comparing their retention times with those of authentic standards and confirmed by analysis of their mass spectral fragmentation patterns.

The results of the fatty acid analysis are shown as follows: Clone hydroxy fatty acid (ricinoleic plus densipolic) as percent of total fatty acids

| | |
|---|---|
| 104-1S | 19.6% |
| 104-1L | 10.9% |
| 104-2P | 10.6% |

Preparation of Antibodies to Oleate Hydroxylase

Antibodies were prepared against the castor oleate hydroxylase, and specifically, against the carboxyl third of the enzyme. This was accomplished by adding a methionine to the sequence from the enzyme starting QHTHP (the Q being residue 277 in the castor oleate hydroxylase). The C-terminus was the authentic C-terminal sequence, RNKY (the Y being 387 for the castor hydroxylase). Rabbits were inoculated with approximately 200 ug of polypeptide followed by four boosts using 100 ug spaced at 2 to four week intervals. Antisera were isolated and the antibody fraction corresponding to the antigen was purified by HPLC-immunoaffinity chromatography in which the antigen was immobilized on an HPLC matrix.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in material science, chemistry, and molecular biology or related fields are intended to be within the scope of the following claims.

What is claimed is:

1. An isolated nucleic acid sequence comprising SEQ ID NO: 1.

2. An isolated nucleic acid sequence encoding SEQ ID NO: 2.

3. A recombinant DNA molecule comprising the nucleic acid sequence of claim 1 operably linked to at least one suitable regulatory sequence.

4. A recombinant DNA molecule comprising the nucleic acid sequence of claim 2 operably linked to at least one suitable regulatory sequence.

5. An expression vector comprising the recombinant DNA molecule of claim 3.

6. An microrganism transformed with the recombinant DNA molecule of claim 3.

7. A plant transformed with the recombinant DNA molecule of claim 3.

8. The transgenic plant of claim 7, wherein the plant is selected from the group consisting of soybean (*Glycine max*), rapeseed and canola (including *Brassica napus* and *B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*) and peanut (*Arachis hypogaea*).

9. A plant cell transformed with the recombinant DNA molecule of claim 3.

10. A plant seed transformed with the recombinant DNA molecule of claim 3.

11. An expression vector comprising the recombinant DNA molecule of claim 4.

12. An microrangism transformed with the recombinant DNA molecule of claim 4.

13. A plant transformed with the recombinant DNA molecule of claim 4.

14. The transgenic plant of claim 13, wherein the plant is selected from the group consisting of soybean (*Glycine max*), rapeseed and canola (including *Brassica napus* and *B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*) and peanut (*Arachis hypogaea*).

15. A plant cell transformed with the recombinant DNA molecule of claim 4.

16. A plant seed transformed with the recombinant DNA molecule of claim 4.

17. A method of producing a plant hydroxylase in a transgenic plant, comprising:
    a) providing an plant transformed with the recombinant DNA molecule of claim 4;
    b) growing the plant under conditions such that a hydroxylase encoded by SEQ ID NO: 1 is expressed.

18. The method of claim 17, wherein the recombinant DNA molecule is integrated into the genome of the plant.

19. A plant produced by the method of claim 17, which produces said plant hydroxylase.

20. A method of producing a plant hydroxylase in a transgenic plant, comprising:
    a) providing an plant transformed with the recombinant DNA molecule of claim 5;
    b) growing the plant under conditions such that a hydroxylase encoded by SEQ ID NO: 1 is expressed.

21. The method of claim 20, wherein the recombinant DNA molecule is integrated into the genome of the plant.

22. A plant produced by the method of claim 20, which produces said plant hydroxylase.

23. A method for altering the phenotype of a plant comprising:
    a) providing:
        i) a vector comprising a nucleic acid sequence encoding a protein, where the nucleic acid sequence is selected from the group consisting of SEQ ID NO:1 and a nucleic acid sequence which encodes SEQ ID NO:2;
        ii) a plant or a plant tissue or a plant cell;
    b) transfecting the plant or plant tissue or plant cell with the vector under conditions such that the protein is expressed in a plant obtained from the plant or plant tissue or plant cell.

* * * * *

SEQUENCE LISTING

```
<160> NUMBER OF SEQ ID NOS: 6

<210> SEQ ID NO 1
<211> LENGTH: 1164
<212> TYPE: DNA
<213> ORGANISM: Ricinus communis
<220> FEATURE:
<221> NAME/KEY: CDS
<222> LOCATION: (1)..(1164)
<223> OTHER INFORMATION:

<400> SEQUENCE: 1 atg gga ggt ggt ggt cgc atg tct act gtc ata acc agc aac aac agt        48
Met Gly Gly Gly Gly Arg Met Ser Thr Val Ile Thr Ser Asn Asn Ser
1               5                   10                  15 gag aag aaa gga gga agc agc cac ctt aag cga gcg ccg cac acg aag        96
Glu Lys Lys Gly Gly Ser Ser His Leu Lys Arg Ala Pro His Thr Lys
            20                  25                  30 cct cct ttc aca ctt ggt gac ctc aag aga gcc atc cca ccc cat tgc       144
Pro Pro Phe Thr Leu Gly Asp Leu Lys Arg Ala Ile Pro Pro His Cys
        35                  40                  45
```

```
ttt gaa cgc tct ttt gtg cgc tca ttc tcc tat gtt gcc tat gat gtc      192
Phe Glu Arg Ser Phe Val Arg Ser Phe Ser Tyr Val Ala Tyr Asp Val
 50                  55                  60 tgc tta agt ttt ctt ttc tac tcg atc gcc acc aac ttc ttc cct tac      240
Cys Leu Ser Phe Leu Phe Tyr Ser Ile Ala Thr Asn Phe Phe Pro Tyr
 65                  70                  75                  80 atc tct tct ccg ctc tcg tat gtc gct tgg ctg gtt tac tgg ctc ttc      288
Ile Ser Ser Pro Leu Ser Tyr Val Ala Trp Leu Val Tyr Trp Leu Phe
                 85                  90                  95 caa ggc tgc att ctc act ggt ctt tgg gtc atc ggc cat gaa tgt ggc      336
Gln Gly Cys Ile Leu Thr Gly Leu Trp Val Ile Gly His Glu Cys Gly
            100                 105                 110 cat cat gct ttt agt gag tat cag ctg gct gat gac att gtt ggc cta      384
His His Ala Phe Ser Glu Tyr Gln Leu Ala Asp Asp Ile Val Gly Leu
            115                 120                 125 att gtc cat tct gca ctt ctg gtt cca tat ttt tca tgg aaa tat agc      432
Ile Val His Ser Ala Leu Leu Val Pro Tyr Phe Ser Trp Lys Tyr Ser
130                 135                 140 cat cgc cgc cac cat tct aac ata gga tct ctc gag cga gac gaa gtg      480
His Arg Arg His His Ser Asn Ile Gly Ser Leu Glu Arg Asp Glu Val
145                 150                 155                 160 ttc gtc ccg aaa tca aag tcg aaa att tca tgg tat tct aag tac tta      528
Phe Val Pro Lys Ser Lys Ser Lys Ile Ser Trp Tyr Ser Lys Tyr Leu
                165                 170                 175 aac aac ccg cca ggt cga gtt ttg aca ctt gct gcc acg ctc ctc ctt      576
Asn Asn Pro Pro Gly Arg Val Leu Thr Leu Ala Ala Thr Leu Leu Leu
            180                 185                 190 ggc tgg cct tta tac tta gct ttc aat gtc tct ggt aga cct tac gat      624
Gly Trp Pro Leu Tyr Leu Ala Phe Asn Val Ser Gly Arg Pro Tyr Asp
            195                 200                 205 cgc ttt gct tgc cat tat gat ccc tat ggc cca ata ttt tcc gaa aga      672
Arg Phe Ala Cys His Tyr Asp Pro Tyr Gly Pro Ile Phe Ser Glu Arg
210                 215                 220 gaa agg ctt cag att tac att gct gac ctc gga atc ttt gcc aca acg      720
Glu Arg Leu Gln Ile Tyr Ile Ala Asp Leu Gly Ile Phe Ala Thr Thr
225                 230                 235                 240 ttt gtg ctt tat cag gct aca atg gca aaa ggg ttg gct tgg gta atg      768
Phe Val Leu Tyr Gln Ala Thr Met Ala Lys Gly Leu Ala Trp Val Met
                245                 250                 255 cgt atc tat ggg gtg cca ttg ctt att gtt aac tgt ttc ctt gtt atg      816
Arg Ile Tyr Gly Val Pro Leu Leu Ile Val Asn Cys Phe Leu Val Met
            260                 265                 270 atc aca tac ttg cag cac act cac cca gct att cca cgc tat ggc tca      864
Ile Thr Tyr Leu Gln His Thr His Pro Ala Ile Pro Arg Tyr Gly Ser
            275                 280                 285 tcg gaa tgg gat tgg ctc cgg gga gca atg gtg act gtc gat aga gat      912
Ser Glu Trp Asp Trp Leu Arg Gly Ala Met Val Thr Val Asp Arg Asp
290                 295                 300 tat ggg gtg ttg aat aaa gta ttc cat aac att gca gac act cat gta      960
Tyr Gly Val Leu Asn Lys Val Phe His Asn Ile Ala Asp Thr His Val
305                 310                 315                 320 gct cat cat ctc ttt gct aca gtg cca cat tac cat gca atg gag gcc     1008
Ala His His Leu Phe Ala Thr Val Pro His Tyr His Ala Met Glu Ala
                325                 330                 335 act aaa gca atc aag cct ata atg ggt gag tat tac cgg tat gat ggt     1056
Thr Lys Ala Ile Lys Pro Ile Met Gly Glu Tyr Tyr Arg Tyr Asp Gly
            340                 345                 350
```

```
acc cca ttt tac aag gca ttg tgg agg gag gca aag gag tgc ttg ttc      1104
Thr Pro Phe Tyr Lys Ala Leu Trp Arg Glu Ala Lys Glu Cys Leu Phe
        355                 360                 365 gtc gag cca gat gaa gga gct cct aca caa ggc gtt ttc tgg tac cgg      1152
Val Glu Pro Asp Glu Gly Ala Pro Thr Gln Gly Val Phe Trp Tyr Arg
370                 375                 380 aac aag tat taa                                                      1164
Asn Lys Tyr
385

<210> SEQ ID NO 2
<211> LENGTH: 387
<212> TYPE: PRT
<213> ORGANISM: Ricinus communis

<400> SEQUENCE: 2
```

Met Gly Gly Gly Arg Met Ser Thr Val Ile Thr Ser Asn Asn Ser
1               5                   10                  15

Glu Lys Lys Gly Gly Ser Ser His Leu Lys Arg Ala Pro His Thr Lys
                20                  25                  30

Pro Pro Phe Thr Leu Gly Asp Leu Lys Arg Ala Ile Pro Pro His Cys
            35                  40                  45

Phe Glu Arg Ser Phe Val Arg Ser Phe Ser Tyr Val Ala Tyr Asp Val
50                  55                  60

Cys Leu Ser Phe Leu Phe Tyr Ser Ile Ala Thr Asn Phe Phe Pro Tyr
65                  70                  75                  80

Ile Ser Ser Pro Leu Ser Tyr Val Ala Trp Leu Val Tyr Trp Leu Phe
                85                  90                  95

Gln Gly Cys Ile Leu Thr Gly Leu Trp Val Ile Gly His Glu Cys Gly
                100                 105                 110

His His Ala Phe Ser Glu Tyr Gln Leu Ala Asp Asp Ile Val Gly Leu
            115                 120                 125

Ile Val His Ser Ala Leu Leu Val Pro Tyr Phe Ser Trp Lys Tyr Ser
130                 135                 140

His Arg Arg His His Ser Asn Ile Gly Ser Leu Glu Arg Asp Glu Val
145                 150                 155                 160

Phe Val Pro Lys Ser Lys Ser Lys Ile Ser Trp Tyr Ser Lys Tyr Leu
                165                 170                 175

Asn Asn Pro Pro Gly Arg Val Leu Thr Leu Ala Ala Thr Leu Leu Leu
            180                 185                 190

Gly Trp Pro Leu Tyr Leu Ala Phe Asn Val Ser Gly Arg Pro Tyr Asp
        195                 200                 205

Arg Phe Ala Cys His Tyr Asp Pro Tyr Gly Pro Ile Phe Ser Glu Arg
210                 215                 220

Glu Arg Leu Gln Ile Tyr Ile Ala Asp Leu Gly Ile Phe Ala Thr Thr
225                 230                 235                 240

Phe Val Leu Tyr Gln Ala Thr Met Ala Lys Gly Leu Ala Trp Val Met
                245                 250                 255

Arg Ile Tyr Gly Val Pro Leu Leu Ile Val Asn Cys Phe Leu Val Met
            260                 265                 270

Ile Thr Tyr Leu Gln His Thr His Pro Ala Ile Pro Arg Tyr Gly Ser
        275                 280                 285

Ser Glu Trp Asp Trp Leu Arg Gly Ala Met Val Thr Val Asp Arg Asp
290                 295                 300

```
Tyr Gly Val Leu Asn Lys Val Phe His Asn Ile Ala Asp Thr His Val
305                 310                 315                 320

Ala His His Leu Phe Ala Thr Val Pro His Tyr His Ala Met Glu Ala
                325                 330                 335

Thr Lys Ala Ile Lys Pro Ile Met Gly Glu Tyr Tyr Arg Tyr Asp Gly
            340                 345                 350

Thr Pro Phe Tyr Lys Ala Leu Trp Arg Glu Ala Lys Glu Cys Leu Phe
        355                 360                 365

Val Glu Pro Asp Glu Gly Ala Pro Thr Gln Gly Val Phe Trp Tyr Arg
    370                 375                 380

Asn Lys Tyr
385

<210> SEQ ID NO 3
<211> LENGTH: 60
<212> TYPE: DNA
<213> ORGANISM: Artificial Sequence
<220> FEATURE:
<223> OTHER INFORMATION: Synthetic

<400> SEQUENCE: 3
gatcaagctt cccgggccat gggaggtggt ggtcgcatgt ctactgtcat aaccagcaac      60

<210> SEQ ID NO 4
<211> LENGTH: 71
<212> TYPE: DNA
<213> ORGANISM: Artificial Sequence
<220> FEATURE:
<223> OTHER INFORMATION: Synthetic

<400> SEQUENCE: 4
gatcgagctc ggatccttaa tacttgttcc ggtaccagaa aacgccttgt gtagggcgtc      60
cttcatctgg c                                                          71

<210> SEQ ID NO 5
<211> LENGTH: 60
<212> TYPE: DNA
<213> ORGANISM: Artificial Sequence
<220> FEATURE:
<223> OTHER INFORMATION: Synthetic

<400> SEQUENCE: 5
gatcaagctt cccgggccat gggaggtggt ggtcgcatgt ctactgccat aaccagcaac      60

<210> SEQ ID NO 6
<211> LENGTH: 71
<212> TYPE: DNA
<213> ORGANISM: Artificial Sequence
<220> FEATURE:
<223> OTHER INFORMATION: Synthetic

<400> SEQUENCE: 6
gatcgagctc ggatccttaa tacttgttcc ggtaccagaa agcgccttgt gtagggcgtc      60
cttcatctgg c                                                          71
```